US012577614B2

(12) United States Patent
Huang et al.

(10) Patent No.: US 12,577,614 B2
(45) Date of Patent: Mar. 17, 2026

(54) KITS AND METHODS FOR DETERMINING COPY NUMBER OF MOUSE TCR GENE

(71) Applicant: SHANGHAI ABELZETA LTD., Shanghai (CN)

(72) Inventors: Jiaqi Huang, Rockville, MD (US); Yihong Yao, Rockville, MD (US); Lin Guo, Shanghai (CN); Jiaxu Yan, Shanghai (CN); Xin Yao, Rockville, MD (US); Shigui Zhu, Rockville, MD (US); Fei Wang, Shanghai (CN); Junfeng Wu, Shanghai (CN); Jishun Lu, Shanghai (CN); Jiaqiang Ren, Shanghai (CN); Li Zhang, Shanghai (CN)

(73) Assignee: Shanghai AbelZeta Ltd., Shanghai (CN)

( * ) Notice: Subject to any disclaimer, the term of this patent is extended or adjusted under 35 U.S.C. 154(b) by 650 days.

(21) Appl. No.: 17/998,844

(22) PCT Filed: May 17, 2021

(86) PCT No.: PCT/US2021/032744
§ 371 (c)(1),
(2) Date: Nov. 15, 2022

(87) PCT Pub. No.: WO2021/236508
PCT Pub. Date: Nov. 25, 2021

(65) Prior Publication Data
US 2023/0193370 A1 Jun. 22, 2023

(30) Foreign Application Priority Data
May 18, 2020 (CN) .......................... 202010423994.3

(51) Int. Cl.
*C12Q 1/6858* (2018.01)
*A61K 40/11* (2025.01)
*A61K 40/32* (2025.01)
*A61K 40/42* (2025.01)
*C12Q 1/6851* (2018.01)

(52) U.S. Cl.
CPC ........... *C12Q 1/6858* (2013.01); *A61K 40/11* (2025.01); *A61K 40/32* (2025.01); *A61K 40/4265* (2025.01); *C12Q 1/6851* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 6,773,882 B2 * | 8/2004 | Hogan | ................. | C12Q 1/6895 435/6.15 |
| 9,113,616 B2 | 8/2015 | Macdonald et al. | | |
| 9,279,122 B2 | 3/2016 | Jakobsen et al. | | |
| 2013/0288237 A1 | 10/2013 | Robins et al. | | |
| 2017/0290858 A1 | 10/2017 | Zhao et al. | | |
| 2018/0327473 A1 | 11/2018 | He et al. | | |
| 2020/0131564 A1 | 4/2020 | Jiang et al. | | |

FOREIGN PATENT DOCUMENTS

| | | |
|---|---|---|
| CN | 102083999 A | 6/2011 |
| CN | 102618646 A | 8/2012 |
| CN | 105377886 A | 3/2016 |
| CN | 107829145 A | 3/2018 |
| CN | 107858400 A | 3/2018 |
| CN | 110117675 A | 8/2019 |
| JP | 2017536825 A1 | 12/2017 |
| JP | 2019535313 A1 | 12/2019 |
| WO | 2006/016113 A1 | 2/2006 |
| WO | 2016/085904 A1 | 6/2016 |
| WO | 2018208553 A1 | 11/2018 |
| WO | 2019/010486 A1 | 1/2019 |

OTHER PUBLICATIONS

Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
International Search Report and Written Opining of PCT/US2021/032744, mailed on Sep. 28, 2021.
Wright et al.: "Quantitative PCR for detection of the OT-1 transgene": BMC Immunology, 2005, 6:20.
He et al.: "Inhibitory Effects of Anti-C II TA RNase P on Major Histocompatibility Complex Class II Antigens' Expression in Daudi Cells", Chinese Journal of Biochemistry and Molecular Biology, 2007, 23(5): pp. 405-409.
Abramson et al., "Nucleic acid amplification technologies", Current Opinion in Biotechnology, 1993; 4:41-47. [7 pages].
Hsuih et al. "Novel, Ligation-Dependent PCR Assay for Detection of Hepatitis C Virus in Serum", J. Clin. Micro. 34(3):501-507 (1996) [7 pages].

* cited by examiner

*Primary Examiner* — Katherine D Salmon
(74) *Attorney, Agent, or Firm* — LEASON ELLIS LLP

(57) ABSTRACT

The present disclosure provides systems, kits and methods for determining the copy number of a mouse TCR transgene. The primers are specific to the conserved regions of the mouse TCR gene. The primers/probes provide good amplification efficiency and can quickly and accurately determine the copy number of a mouse TCR transgene.

13 Claims, 27 Drawing Sheets

Specification includes a Sequence Listing.

A1

B1

C1

D1

A1

B1

C1

Cycle Number (Ct)

Copy Number

D1

A1

C1

D1

SEQUENCE LISTING

<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gggaagggca gactgtgg                                                18

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
gcaggatctc gtacaggatt gtg                                          23

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
catcaccagc gcctcctatc a                                                        21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
cgagatcgcc aacaagagga a                                                        21

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
tgcacctcct tgccattca                                                          19

<210> SEQ ID NO 6
<211> LENGTH: 17
<212> TYPE: DNA
<213> ORGANISM: Artificial Sequence
<220> FEATURE:
<223> OTHER INFORMATION: Synthetic

<400> SEQUENCE: 6
cccaccagga cagctcc                                                            17

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
tgcctgttca ccgactttga tag                                                     23

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
cacggtcttg tctgtgataa aggt                                                    24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
cagatcaatg tgcctaagac aatg                                                    24

<210> SEQ ID NO 10

-continued

```
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgccaccctg acagagaaga                                                    20

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
gcccatcacg gacaggtt                                                      18

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
acagacatga acctgaattt t                                                  21

<210> SEQ ID NO 13
<211> LENGTH: 924
<212> TYPE: DNA
<213> ORGANISM: Mus musculus

<400> SEQUENCE: 13
gacctgcgca atgtgacccc ccctaaggtg tccctgttcg agccttctaa ggccgagatc     60
gccaacaaga ggaaggccac cctggtgtgc ctggcaaggg gcttctttcc agatcacgtg    120
gagctgtcct ggtgggtgaa tggcaaggag gtgcactctg gcgtgagcac agaccccag     180 gcctacaagg agtccaacta ttcttactgc ctgtctagcc ggctgagagt gagcgccacc    240
ttttggcaca accccaggaa tcacttccgc tgtcaggtgc agtttcacgg cctgtccgag    300
gaggataagt ggcctgaggg ctctcccaag cctgtgacac agaacatcag cgccgaggca    360
tggggaaggg cagactgtgg catcaccagc gcctcctatc agcagggcgt gctgagcgcc    420
acaatcctgt acgagatcct gctgggcaag gccaccctgt atgctgtgct ggtgtcaact    480
ctggtggtca tggctatggt gaaacggaaa aactccatcc agaatccaga gcccgccgtg    540
tatcagctga aggacccacg gagccaggat agcaccctgt gcctgttcac cgactttgat    600
agccagatca atgtgcctaa gacaatggag tccggcacct ttatcacaga caagaccgtg    660
ctggatatga aggccatgga cagcaagtcc aacggcgcca tcgcctggtc taatcagaca    720
agcttcacct gccaggatat ctttaaggag acaaacgcca cctacccatc tagcgacgtg    780
ccctgtgatg ccaccctgac agagaagagc ttcgagacag acatgaacct gaatttttcag    840 aacctgtccg tgatgggcct gagaatcctg ctgctgaagg tggccggctt caatctgctg    900
atgacactgc gcctgtggtc ctct                                           924
```

KITS AND METHODS FOR DETERMINING COPY NUMBER OF MOUSE TCR GENE

CROSS REFERENCE TO RELATED APPLICATION

The present application claims priority to Chinese patent application No. 2020104239943, filed May 18, 2020, which is hereby incorporated by reference in its entirety.

SEQUENCE LISTING

This application contains a Sequence Listing which has been filed electronically in ASCII format and is hereby incorporated by reference in its entirety. Said ASCII copy, created on May 17, 2021, is named 11299-009940-WO0_ST25.txt and is 4 KB in size.

TECHNICAL FIELD

The present disclosure relates to the fields of sequence analysis and bioinformatics, specifically to kits and methods for determining the copy number of a mouse T cell receptor (TCR) gene.

BACKGROUND

The T cell receptor (TCR) is a protein complex on the surface of T cells that specifically recognizes and binds an antigen peptide-MHC (major histocompatibility complex) complex. The TCR generally is present in the form of a complex with a CD3 molecule. Some TCRs are composed of α and β peptide chains while some are composed of γ and δ peptide chains.

When human tumor-specific antigens are used to immunize HLA-transgenic mice, high-affinity mouse TCRs that can recognize human tumor-specific antigens can be discovered. It is an important method for screening TCRs with a therapeutic value.

The TCR-T therapy has shown broad prospects in the treatment of solid tumors. However, out of consideration of the biological safety of genetically engineered cells, the FDA stipulates that in genetically engineered cells, the transgene cannot exceed five copies per cell. This indicates that in the quality monitoring and production of TCR-T, it is necessary to quickly and accurately determine the copy number of the transgene. In an animal test of TCR-T, identifying the copy number of human TCR gene in an animal sample (tissue or blood) can reflect the amplification and proliferation conditions of TCR-T in the test animal. In TCR-T clinical trials, determining the copy number of exogenous TCR genes in the test sample (tissue or blood) can reflect the amplification and proliferation conditions of TCR-T in the subject, which can be used as a key pharmacokinetic (PK) index for the TCR-T treatment.

At present, there is no relevant report on the detection of TCR gene copies. Therefore, with the widespread use of mouse TCR screening and the development of clinical products, it is necessary to develop a method that can quickly and accurately determine the copy number of a mouse TCR transgene.

SUMMARY

The present disclosure provides for a system or kit for determining the copy number of a mouse T cell receptor (TCR) gene. The system or kit may comprise one or more primer pairs selected from a first primer pair, a second primer pair, a third primer pair and a fourth primer pair.

The first primer pair may comprise (or consist essentially of, or consist of) (i) a primer comprising (or having, or consisting essentially of, or consisting of) a nucleic acid sequence about 80% to about 100% identical to the nucleic acid sequence set forth in SEQ ID NO:1, and (ii) a primer comprising (or having, or consisting essentially of, or consisting of) a nucleic acid sequence about 80% to about 100% identical to the nucleic acid sequence set forth in SEQ ID NO:2.

The second primer pair may comprise (or consist essentially of, or consist of) (i) a primer comprising (or having, or consisting essentially of, or consisting of) a nucleic acid sequence about 80% to about 100% identical to the nucleic acid sequence set forth in SEQ ID NO:4, and (ii) a primer comprising (or having, or consisting essentially of, or consisting of) a nucleic acid sequence about 80% to about 100% identical to the nucleic acid sequence set forth in SEQ ID NO:5.

The third primer pair may comprise (or consist essentially of, or consist of) (i) a primer comprising (or having, or consisting essentially of, or consisting of) a nucleic acid sequence about 80% to about 100% identical to the nucleic acid sequence set forth in SEQ ID NO: 7 and (ii) a primer comprising (or having, or consisting essentially of, or consisting of) a nucleic acid sequence about 80% to about 100% identical to the nucleic acid sequence set forth in SEQ ID NO: 8.

The fourth primer pair may comprise (or consist essentially of, or consist of) (i) a primer comprising (or having, or consisting essentially of, or consisting of) a nucleic acid sequence about 80% to about 100% identical to the nucleic acid sequence set forth in SEQ ID NO:10, and (ii) a primer comprising (or having, or consisting essentially of, or consisting of) a nucleic acid sequence about 80% to about 100% identical to the nucleic acid sequence set forth in SEQ ID NO: 11.

The system or kit may further comprise one or more probes selected from a first probe, a second probe, a third probe, and a fourth probe.

The first probe, second probe, third probe, or fourth probe may be a TaqMan probe.

The first probe may comprise (or have, or consist essentially of, or consist of) a nucleic acid sequence about 80% to about 100% identical to the nucleic acid sequence set forth in SEQ ID NO: 3.

The second probe may comprise (or have, or consist essentially of, or consist of) a nucleic acid sequence about 80% to about 100% identical to the nucleic acid sequence set forth in SEQ ID NO: 6.

The third probe may comprise (or have, or consist essentially of, or consist of) a nucleic acid sequence about 80% to about 100% identical to the nucleic acid sequence set forth in SEQ ID NO: 9.

The fourth probe may comprise (or have, or consist essentially of, or consist of) a nucleic acid sequence about 80% to about 100% identical to the nucleic acid sequence set forth in SEQ ID NO: 12.

In certain embodiments, the system or kit may comprise one or more of the following primer/probe set: the first primer pair and the first probe; the second primer pair and the second probe; the third primer pair and the third probe; and the fourth primer pair and the fourth probe.

In certain embodiments, the system or kit may comprise the first primer pair and the first probe.

The present disclosure provides for a method for determining the copy number of a mouse T cell receptor (TCR) gene in a sample. The method may comprise: (a) contacting the sample with the present system or kit; and (b) conducting a nucleic acid amplification reaction.

In certain embodiments, the mouse TCR gene is a transgene.

In certain embodiments, the nucleic acid amplification reaction is polymerase chain reaction (PCR).

An object of the present disclosure is to provide a reagent for determining the copy number of a mouse TCR transgene, which can quickly and accurately determine the copy number of the mouse TCR transgene.

In a first aspect of the present disclosure, a kit for determining the copy number of a mouse TCR transgene is provided. The kit comprises a primer pair and a TaqMan probe for conserved regions of mouse TCR gene, and the primers are selected from the group consisting of:

(i) A first primer pair (D1), comprising a primer with a sequence as shown in SEQ ID NO:1 and a primer with a sequence as shown in SEQ ID NO:2;

(ii) A second primer pair (A1), comprising a primer with a sequence as shown in SEQ ID NO:4 and a primer with a sequence as shown in SEQ ID NO:5; and (iii) A combination of the first primer pair and the second primer pair.

In certain embodiments, the primer pair is the first primer pair, and the kit further comprises a first TaqMan probe comprising a sequence as shown in SEQ ID NO: 3.

In certain embodiments, the primer pair is the second primer pair, and the kit further comprises a second TaqMan probe comprising a sequence as shown in SEQ ID NO:6.

In certain embodiments, the kit further comprises a primer pair selected from the group consisting of:

(iii) A third primer pair (B1), comprising a primer with a sequence as shown in SEQ ID NO: 7 and a primer with a sequence as shown in SEQ ID NO: 8; and (iv) A fourth primer pair (C1), comprising a primer with a sequence as shown in SEQ ID NO:10 and a primer with a sequence as shown in SEQ ID NO: 11.

In certain embodiments, the primer pair is a third primer pair, and the kit further comprises a third TaqMan probe comprising a sequence as shown in SEQ ID NO:9.

In certain embodiments, the primer pair is a fourth primer pair, and the kit further comprises a fourth TaqMan probe comprising a sequence as shown in SEQ ID NO:12.

In certain embodiments, a 5 'end of the TaqMan probe is labeled with a fluorescent reporter, and a 3' end is labeled with a fluorescent quencher. Alternatively, a 3' end of the TaqMan probe is labeled with a fluorescent reporter, and a 5' end of the TaqMan probe is labeled with a fluorescent quencher.

In certain embodiments, the fluorescent reporter may be FAM and VIC, while the quencher may be MGB and TAMRA.

In certain embodiments, the fluorescent reporter is FAM, while the quencher is MGB.

In a second aspect of the present disclosure, a reagent combination for determining the copy number of a mouse TCR transgene is provided. The reagent combination comprises a first primer pair and a first TaqMan probe, the first primer pair comprises a primer with a sequence as shown in SEQ ID NO:1 and a primer with a sequence as shown in SEQ ID NO:2, and the sequence of the first TaqMan probe is as shown in SEQ ID NO:3.

In a third aspect of the present disclosure, a reagent combination for determining the copy number of a mouse TCR transgene is provided. The reagent combination comprises a second primer pair and a second TaqMan probe, the second primer pair comprises a primer with a sequence as shown in SEQ ID NO: 4 and a primer with a sequence as shown in SEQ ID NO: 5, and the sequence of the second TaqMan probe is as shown in SEQ ID NO:6.

In a fourth aspect of the present disclosure, a use of the kit according to the first aspect of the present disclosure or the reagent combination according to the second or third aspect of the present disclosure is provided. The kit or reagent combination is used to prepare a testing product for quality control of mouse TCR.

In a fifth aspect of the present disclosure, a method for in vitro quality control of mouse TCR is provided. The method may comprise the steps of:

(a) providing a sample to be tested;

(b) using a primer pair and a TaqMan probe for the conserved regions of the mouse TCR gene to perform polymerase chain reaction (PCR) amplification on the sample to be tested, thereby determining the copy number of a TCR transgene; and (c) evaluating the quality of the sample to be tested based on the determined copy number of the TCR transgene.

In certain embodiments, the primer concentration is 0.45 $\mu$M and the probe concentration is 0.125 $\mu$M.

In certain embodiments, the minimum number of the copies of the standard product is 10, or the minimum copy number point is 10 copies.

In certain embodiments, the method is non-diagnostic and non-therapeutic.

In certain embodiments, in step (b), a first primer pair and a first TaqMan probe are used.

In certain embodiments, in step (b), (Y1) a first primer pair and a first TaqMan probe and (Y3) an RNase P reference gene primer/probe are used at the same time.

In certain embodiments, in step (b), single-plex or multiplex (e.g., duplex) PCR amplification is used.

In certain embodiments, in step (b), a second primer pair and a second TaqMan probe are used.

In certain embodiments, in step (b), a third primer pair and a third TaqMan probe are used.

In certain embodiments, in step (b), a fourth primer pair and a fourth TaqMan probe are used.

In certain embodiments, in step (b), (Y1) a first primer pair and a first TaqMan probe and (Y2) a second primer pair and a second TaqMan probe are used simultaneously or successively for PCR amplification.

In certain embodiments, in step (b), by comparing the Ct (threshold cycle) value, the copy number of the TCR transgene are determined.

In certain embodiments, in step (b), the Ct value of the sample to be tested is compared with a standard value or a standard curve to determine the copies of the TCR transgene.

In certain embodiments, the sample to be tested includes a nucleic acid sample.

In certain embodiments, the nucleic acid sample is the total nucleic acids extracted from M cells, where M is a positive integer. For example, M is 1, 2, 3, 4, 5, 6, 7, 8, 9 or 10.

In certain embodiments, step (b) comprises steps of:

S1) selecting a conserved region of the mouse TCR gene as a target gene fragment;

S2) inserting the target gene fragment into a vector to construct a standard plasmid, using it as a standard stock solution, and then performing serial dilutions to obtain a series of the standard substances;

S3) performing real-time fluorescent quantitative PCR (qPCR) on the genes of the standard substance and the sample to be tested, drawing a standard curve based on the Ct values and copy numbers of the standard substances, and obtaining a calculation formula; and S4) bringing the Ct value of the sample to be tested into the calculation formula of the standard curve in step S3) to obtain the gene copies of the sample to be tested.

In certain embodiments, step (b) comprises steps of:

R1) selecting a conserved region of the mouse TCR gene as a target gene fragment and a reference gene with a known sequence;

R2) inserting the target gene fragment into a vector to construct a standard plasmid, using it as a standard stock solution, and then performing serial dilutions to obtain a series of standard substances;

R3) using the reagent according to the first aspect of the present disclosure, performing real-time fluorescent quantitative PCR (qPCR) on the genes of the standard substances and the sample to be tested, drawing a standard curve based on the Ct values and copy numbers of the series of standard substances, and obtaining a calculation formula;

R4) using the Ct value of a reference gene (e.g., the RNaseP gene) to calculate the calibration factor for each sample;

R5) obtaining the copy number of the TCR gene per $\mu$g of the genome in the sample to be tested by comparing with the copy number of the reference gene per $\mu$g of the genome.

In certain embodiments, step (b) further comprises a step of adding human background DNA.

In certain embodiments, the human background DNA is the genomic DNA of a peripheral blood mononuclear cell (PBMC).

In certain embodiments, the amount of the human background DNA is 50 ng.

It should be understood that within the scope of the present disclosure, the foregoing technical features of the present disclosure and the technical features described in detail below (e.g., embodiments) can be combined with each other to form new or preferred technical solutions.

BRIEF DESCRIPTION OF THE DRAWINGS

FIGS. 2-1A, 2-1B, 2-1C and 2-1D show the curves in the absence of background genomic DNA. FIGS. 2-2A, 2-2B, 2-2C and 2-2D show the curves in the presence of background genomic DNA.

FIGS. 4-1, 4-2 and 4-3 show the selection of the lowest copy number points of the standard curves. FIG. 4-1 shows the amplification curves of the points on the standard curves. FIG. 4-2 is a standard curve using 10 copies as the lowest point, and FIG. 4-3 is a standard curve after deleting the 10 copies as the lowest point.

FIGS. 5-1, 5-2 and 5-3 show duplex reaction tests for the D1 primers/probe at different concentrations. FIG. 5-1 shows a test at 1× primer concentration (0.9 $\mu$M primers, 0.25 $\mu$M probe). FIG. 5-2 shows a test at 0.5× concentration (0.45 $\mu$M primers, 0.125 $\mu$M probe). FIG. 5-3 shows a test at 2× primer concentration (1.8 $\mu$M primers, 0.5 $\mu$M probe).

FIGS. 6-1, 6-2 and 6-3 show duplex reaction tests of the D1 primers/probe at different concentrations of background gDNA. FIG. 6-1 shows a test with 100 ng gDNA. FIG. 6-2 shows a test with 50 ng gDNA. FIG. 6-3 shows a test with 25 ng gDNA.

DETAILED DESCRIPTION

Figure 1:
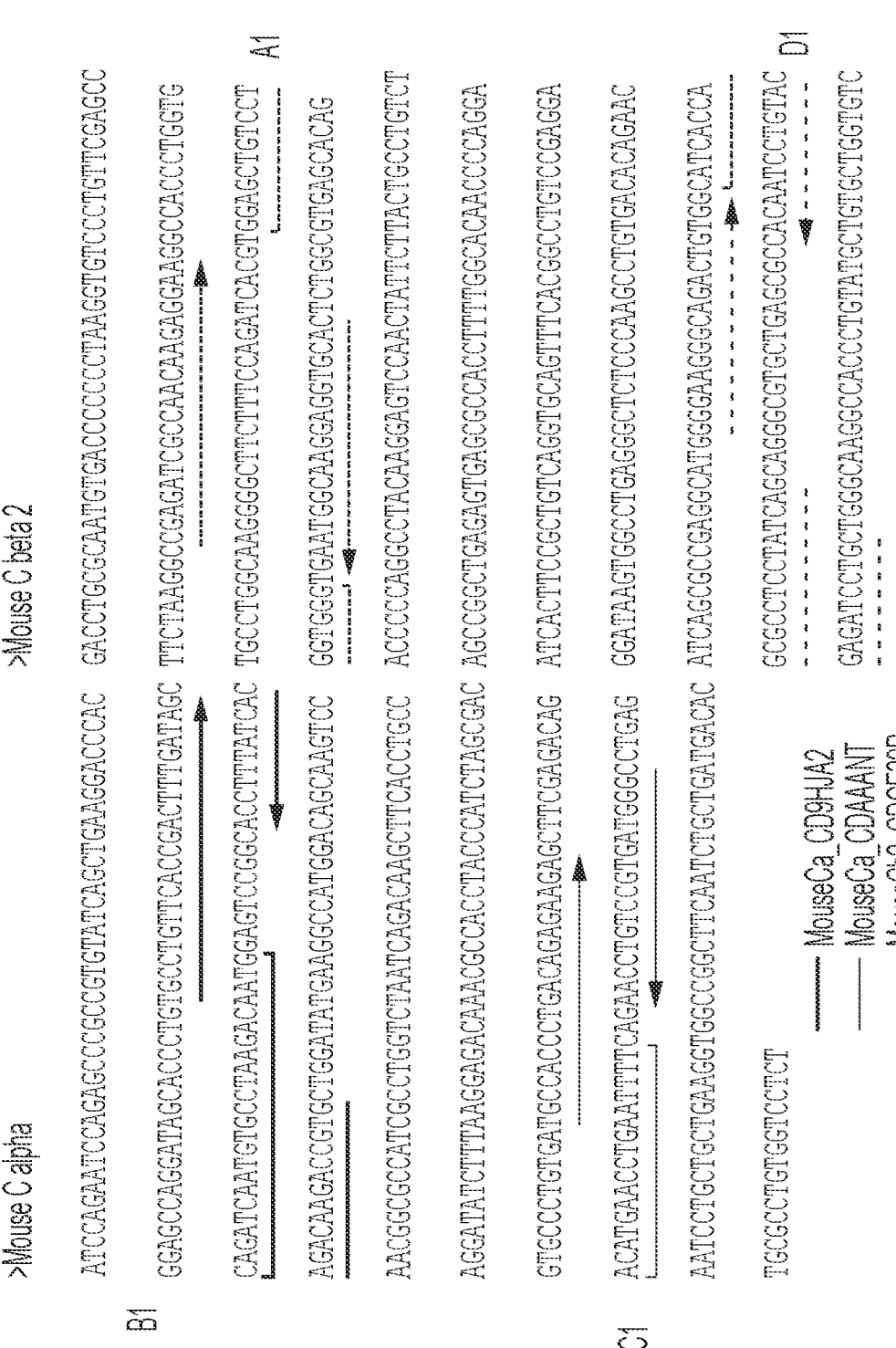
FIG. 1 shows four sets of primers/probes designed according to the sequences of the conserved regions of a mouse TCR gene.

The present systems and methods can quickly and accurately determine the copy number of a mouse TCR transgene. This provides a reliable approach for determining the copy number of the mouse TCR gene in T cells during clinical testing and production.

The present disclosure provides four sets of primers/ TaqMan probes specific to the conserved regions of the mouse TCR gene. In the present method, single-plex reactions of a target gene in the presence or absence of human background DNA may be performed. Duplex reactions of a target gene and a reference gene in the presence or absence of human background DNA may be performed.

The present disclosure provides for a system or kit for determining the copy number of a mouse T cell receptor (TCR) gene. The system or kit may comprise one or more primer pairs selected from a first primer pair, a second primer pair, a third primer pair and a fourth primer pair.

The first primer pair may comprise (or consist essentially of, or consist of) (i) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO:1, and (ii) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleic acid sequence set forth in SEQ ID NO:2.

The second primer pair may comprise (or consist essentially of, or consist of) (i) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO:4, and (ii) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO:5.

The third primer pair may comprise (or consist essentially of, or consist of) (i) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 7 and (ii) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 8.

The fourth primer pair may comprise (or consist essentially of, or consist of) (i) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO:10, and (ii) a primer comprising (or having, or consisting essentially of, or consisting of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 11.

The system or kit may further comprise one or more probes selected from a first probe, a second probe, a third probe, and a fourth probe.

The first probe, second probe, third probe, or fourth probe may be a TaqMan probe.

The first probe may comprise (or have, or consist essentially of, or consist of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 3.

The second probe may comprise (or have, or consist essentially of, or consist of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 6.

The third probe may comprise (or have, or consist essentially of, or consist of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 9.

The fourth probe may comprise (or have, or consist essentially of, or consist of) a nucleic acid sequence about 80% to about 100%, at least or about 70%, at least or about 75%, at least or about 80%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleic acid sequence set forth in SEQ ID NO: 12.

In certain embodiments, the system or kit may comprise one or more of the following primer/probe set: the first primer pair and the first probe; the second primer pair and the second probe; the third primer pair and the third probe; the fourth primer pair and the fourth probe.

In certain embodiments, the system or kit may comprise the first primer pair and the first probe.

The present disclosure provides for a method for determining the copy number of a mouse T cell receptor (TCR)

gene in a sample. The method may comprise: (a) contacting the sample with the present system or kit; and (b) conducting a nucleic acid amplification reaction.

In certain embodiments, the mouse TCR gene is a transgene.

In certain embodiments, the nucleic acid amplification reaction is polymerase chain reaction (PCR).

A primer may be an oligonucleotide that is capable of hybridizing (or annealing) with a nucleic acid and serving as an initiation site for nucleotide (RNA or DNA) polymerization under appropriate conditions (e.g., in an appropriate buffer and at a suitable temperature). A primer may be a polynucleotide that is capable of specifically hybridizing to a target gene (or template), and, in the presence of the template, a polymerase and suitable buffers and reagents, can be extended to form a primer extension product. In some embodiments, the primer is labeled with a detectable moiety. In some embodiments, a primer is not labeled.

A probe may be an oligonucleotide capable of binding to a target nucleic acid of complementary sequence. The probe may be labeled with a detectable label to permit facile detection of the probe. Alternatively, however, the probe may be unlabeled, but may be detectable by specific binding with a ligand that is labeled, either directly or indirectly. Primers may also function as probes. In some embodiments, the probe is a FRET probe. In some embodiments, the probe is a TaqMan probe, a Molecular Beacon, or a Scorpion probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In some embodiments, a probe is extendable.

In some embodiments, a primer or probe is identical to, or complementary to, at least or about 8, at least or about 9, at least or about 10, at least or about 11, at least or about 12, at least or about 13, at least or about 14, at least or about 15, at least or about 16, at least or about 17, at least or about 18, at least or about 19, at least or about 20, at least or about 21, at least or about 22, at least or about 23, at least or about 24, at least or about 25, at least or about 26, at least or about 27, at least or about 28, at least or about 29, or at least or about 30 contiguous nucleotides of a sequence from a target gene. In some embodiments, a primer may also comprise portions or regions that are not identical or complementary to the target gene.

In some embodiments, a region of a primer that is identical or complementary to a target gene is contiguous, such that any region of a primer that is not identical or complementary to the target gene does not disrupt the identical or complementary region. The primer or probe may be at least 90%, at least 91%, at least 92%, at least 93%, at least 94%, at least 95%, at least 96%, at least 97%, at least 98%, at least 99%, or 100% complementary to the target molecule. In certain embodiments, the primer or probe may be at least 65% complementary to the target nucleic acid sequence over a sequence of at least or about 7 nucleotides, over a sequence in the range of 10-30 nucleotides, over a sequence of at least 14-25 nucleotides. In some embodiments, a primer or probe comprises a region that is complementary to a sequence of at least or about 8, at least or about 9, at least or about 10, at least or about 11, at least or about 12, at least or about 13, at least or about 14, at least or about 15, at least or about 16, at least or about 17, at least or about 18, at least or about 19, at least or about 20, at least or about 21, at least or about 22, at least or about 23, at least or about 24, at least or about 25, at least or about 26, at least or about 27, at least or about 28, at least or about 29, or at least or about 30 contiguous nucleotides of a target molecule (e.g., the TCR gene). When a primer or probe comprises a region that is "complementary to at least x contiguous nucleotides of a target molecule," the primer or probe may be at least 95% complementary to at least x contiguous nucleotides of the target molecule. In some embodiments, the primer or probe is at least 96%, at least 97%, at least 98%, at least 99%, or 100% complementary to the target molecule.

The primer or probe may contain from 10 to 30 nucleotides, from 15 to 30 nucleotides, from 15 to 25 nucleotides, from 17 to 24 nucleotides, from 30 to 50 nucleotides, from 7 to 15 nucleotides, from 15 to 20 nucleotides, at least 20, 30, or 40 nucleotides, or at least or about 50, 60, 70, 80, or 90 nucleotides. The primer or probe may have at least or about 7 nucleotides, at least or about 8 nucleotides, at least or about 9 nucleotides, at least or about 10 nucleotides, at least or about 11 nucleotides, at least or about 12 nucleotides, at least or about 13 nucleotides, at least or about 14 nucleotides, at least or about 15 nucleotides, at least or about 16 nucleotides, at least or about 17 nucleotides, at least or about 18 nucleotides, at least or about 19 nucleotides, at least or about 20 nucleotides, at least or about 21 nucleotides, at least or about 22 nucleotides, at least or about 23 nucleotides, at least or about 24 nucleotides, or at least or about 25 nucleotides, at least or about 26 nucleotides, at least or about 27 nucleotides, at least or about 28 nucleotides, at least or about 29 nucleotides, or at least or about 30 nucleotides. In some embodiments, the primer or probe has a sequence with one, two or three base mismatches when compared to the sequence in the target gene or sequence.

In some embodiments, primer pairs are provided. A primer pair is said to be capable of amplifying a nucleic acid if, when used in an amplification reaction, the primer pair produces multiple copies of the nucleic acid. These multiple copies can contain addition nucleotide sequences that are added in an amplification reaction.

In some embodiments, real-time PCR may be performed using a FRET probe, which includes, but is not limited to, a TaqMan probe, a Molecular beacon probe and a Scorpion probe. In some embodiments, the real-time PCR detection and quantification is performed with a TaqMan probe, e.g., a linear probe that typically has a fluorescent dye/label covalently bound at one end of the DNA and a quencher molecule covalently bound at the other end of the DNA. The FRET probe comprises a sequence that is complementary to a region of the target gene such that, when the FRET probe is hybridized to the target gene or an amplicon of the target gene, the dye fluorescence is quenched, and when the probe is digested during amplification of the target gene or amplicon of the target gene, the dye is released from the probe and produces a fluorescence signal. In some embodiments, the presence of the target gene in the sample is detected.

In some embodiments, labels/dyes that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB. Specific examples of labels/dyes also include, but are not limited to, Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET. Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. Examples of fluorescently labeled deoxyribonucleotides useful in the preparation of real-time PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

Nucleic acid amplification reactions may be polymerase chain reaction (PCR), reverse-transcriptase PCR, real-time PCR, nested PCR, multiplex PCR, quantitative PCR (Q-PCR), ligase chain reaction (LCR), transcription-based amplification system (TAS), nucleic acid sequence-based amplification (NASBA), transcription mediated amplification (TMA), strand displacement amplification (SDA), ligation detection reaction (LDR), rolling circle amplification (RCA), hyper-branched RCA (HRCA), multiplex ligation-dependent probe amplification (MLPA), ligation followed by Q-replicase amplification, primer extension, strand displacement amplification (SDA), hyperbranched strand displacement amplification, multiple displacement amplification (MDA), two-step multiplexed amplifications, etc. Nucleic acid amplification reactions may also be multiplex versions and combinations thereof, including, but not limited to, OLA/PCR, PCR/OLA, LDR/PCR, PCR/PCR/LDR, PCR/LDR, LCR/PCR, PCR/LCR (also known as combined chain reaction-CCR), and the like. The nucleic acid amplification reactions may be carried out by multiplex PCR, e.g., multiplex real-time PCR. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr. Opin. Biotechnol. 1993 February; 4(1):41-7.

The term "qPCR" is used herein to refer to quantitative real-time polymerase chain reaction (PCR), which is also known as "real-time PCR" or "kinetic polymerase chain reaction."

Samples comprising nucleic acids may be obtained from biological sources using conventional methods known in the art. In particular, DNA or RNA useful in the methods described herein can be extracted and/or amplified from any source, including bacteria, protozoa, fungi (e.g., yeast), viruses, organelles, as well higher organisms such as plants or animals, particularly mammals, and more particularly humans. Nucleic acids can be extracted or amplified from cells, bodily fluids (e.g., blood, a blood fraction, urine, amniotic fluid, etc.), or tissue samples by any of a variety of standard techniques. Illustrative samples include samples of plasma, serum, blood, spinal fluid, lymph fluid, peritoneal fluid, pleural fluid, oral fluid, the chorionic villi, and external sections of the skin; samples from the respiratory, intestinal genital, and urinary tracts; samples of tears, saliva, blood cells, stem cells, or cancer cells or tissues (e.g., tumors). For example, samples of fetal DNA can be obtained from an embryo (e.g., from one or a few embryonic or fetal cells) or from maternal blood. Samples can be obtained from live or dead organisms or from in vitro cultures. Illustrative samples can include single cells, formalin-fixed paraffin-embedded tissue samples, and needle biopsies. Nucleic acids useful in the methods described herein can also be derived from one or more nucleic acid libraries, including cDNA, cosmid, YAC, BAC, Pl, PAC libraries, and the like.

In certain embodiments, the copy number may be copies of the gene in an amount of genomic DNA (e.g., 1 μg, 50 ng, etc. genomic DNA). In certain embodiments, the copy number may be copies of the gene in a sample. In certain embodiments, the copy number may be copies of the gene per cell or in a population of cells. In certain embodiments, the copy number may be an average copy number of the gene in a population of cells.

In certain embodiments, the copy number may be a relative copy number of a gene (per genome) which may be expressed as the ratio of the copy number of a target polynucleotide/gene to the copy number of a reference polynucleotide/gene in a DNA sample. The reference polynucleotide/gene may be a single copy reference polynucleotide/gene (copy number may be 1). The relative copy number of a polynucleotide/gene (per genome) can be expressed as the ratio of the copy number of a target polynucleotide/gene to the copy number of a reference polynucleotide/gene in a DNA sample. The genomic copy number is known for the reference sequence. As such, target polynucleotide copy number can be analyzed relative to the reference polynucleotide/gene so as to determine the relative copy number of the target polynucleotide/gene. For example, the RNaseP gene is a single-copy gene and may be used as the reference gene in a copy number assay. For illustration, other useful reference sequences include beta-actin, glyceraldehyde-3-phosphate dehydrogenase (GAPDH), hydroxymethylbilane synthase (HMBS), beta-actin, and/or beta-globin; however, it will be appreciated the invention is not limited to a particular reference sequence.

By using two assays for the two genes (the target poly-nucleotide/gene and the reference polynucleotide/gene) with two different labels (e.g., fluorescent dyes) in the same reaction or on the same device, the methods described herein can be used to simultaneously quantitate both genes in the same DNA sample. Alternatively, the target gene can be amplified in one reaction and the reference gene can be assayed in a different reaction and the data compared. The ratio of these two genes is the relative copy number of the target polynucleotide sequence, or gene of interest, in a DNA sample.

The system may be in a composition. In some embodiments, the composition is an aqueous composition. In some embodiments, the aqueous composition comprises a buffering component, such as phosphate, tris, HEPES, etc., and/or additional components, as discussed below. In some embodiments, the composition is dry, for example, lyophilized, and suitable for reconstitution by addition of fluid. A dry composition may include one or more buffering components and/or additional components.

In some embodiments, a composition further comprises one or more additional components. Additional components include, but are not limited to, salts, such as NaCl, KCl, and MgCl$_2$; polymerases, including thermostable polymerases such as Taq; dNTPs; bovine serum albumin (BSA) and the like; reducing agents, such as beta-mercaptoethanol; EDTA and the like; etc. One skilled in the art can select suitable composition components depending on the intended use of the composition.

Kit

In some embodiments, a kit comprises the present system. In some embodiments, a kit comprises at least one primer pair and/or probe discussed above. In some embodiments, a kit further comprises at least one polymerase, such as a thermostable polymerase. In some embodiments, a kit comprises further dNTPs. In some embodiments, kits for use in the real-time PCR methods described herein comprise one or more target gene-specific FRET probes and/or one or more primers for amplification of target genes.

In some embodiments, the kit comprises at least one, at least two, at least three, or at least four sets of primers. In some embodiments, the kit further comprises at least one set of primers for amplifying a reference polynucleotide/gene.

In some embodiments, the kits for use in real-time PCR methods described herein further comprise reagents for use in the amplification reactions. In some embodiments, the kits comprise enzymes such as heat stable DNA polymerase, such as Taq polymerase. In some embodiments, the kits further comprise deoxyribonucleotide triphosphates (dNTP) for use in amplification. In some embodiments, the kits comprise buffers optimized for specific hybridization of the probes and primers.

A kit in the present disclosure may comprise a primer pair and a TaqMan probe for conserved regions of the mouse TCR gene, and the primers are selected from the group consisting of: (i) A first primer pair (D1), comprising a primer with a sequence as shown in SEQ ID NO:1 and a primer with a sequence as shown in SEQ ID NO:2; (ii) A second primer pair (A1), comprising a primer with a sequence as shown in SEQ ID NO:4 and a primer with a sequence as shown in SEQ ID NO:5; and (iii) A combination of the first primer pair and the second primer pair.

In certain embodiments, the primer pair is the first primer pair, and the kit further comprises a first TaqMan probe with a sequence as shown in SEQ ID NO: 3.

In certain embodiments, the primer pair is the second primer pair, and the kit further comprises a second TaqMan probe with a sequence as shown in SEQ ID NO:6.

Optionally, the foregoing kit further comprises a primer pair selected from the group consisting of: (i) A third primer pair (B1), comprising a primer with a sequence as shown in SEQ ID NO: 7 and a primer with a sequence as shown in SEQ ID NO: 8; and (ii) A fourth primer pair (C1), comprising a primer with a sequence as shown in SEQ ID NO:10 and a primer with a sequence as shown in SEQ ID NO: 11.

In certain embodiments, the primer pair is the third primer pair and the kit further comprises a third Taqman probe with a sequence as shown in SEQ ID NO:9.

In certain embodiments, the primer pair is the fourth primer pair and the kit further comprises a fourth Taqman probe with a sequence as shown in SEQ ID NO:12.

In certain embodiments, a 5' end of the Taqman probe is labeled with a fluorescent reporter (e.g., FAM or VIC) and a 3' end is labeled with a fluorescent quencher (e.g., MGB or TAMRA) in the present disclosure. Alternatively, a 3' end of the Taqman probe is labeled with a fluorescent reporter (e.g., FAM or VIC) and a 5' end is labeled with a fluorescent quencher (e.g., MGB or TAMRA).

The kit in the present disclosure may further comprise one or more containers, and the above primer pair and TaqMan probe can be placed in different containers or combined in the same container.

Reagent Combination

The reagent in the present disclosure may refer to a reagent combination for determining the copy number of a mouse TCR transgene.

The reagent in the present disclosure may comprise a first primer pair and a first TaqMan probe, where the first primer pair comprises a primer with a sequence as shown in SEQ ID NO:1 and a primer with a sequence as shown in SEQ ID NO:2, and the sequence of the first TaqMan probe is as shown in SEQ ID NO:3; and/or a second primer pair and a second TaqMan probe, where the second primer pair comprises a primer with a sequence as shown in SEQ ID NO: 4 and a primer with a sequence as shown in SEQ ID NO: 5, and the sequence of the second TaqMan probe is as shown in SEQ ID NO:6; and/or an RNase P reference gene primer/probe.

Method for Determining Mouse TCR Gene Copy Number

The present method may comprise the steps of:

(a) providing a sample to be tested;

(b) using a primer pair and a TaqMan probe for conserved regions of mouse TCR gene to perform PCR amplification on the sample to be tested, thereby determining the copy number of a TCR transgene; and (c) evaluating the quality of the sample to be tested based on the determined copy number of the TCR transgene.

In step (b), a first primer pair and a first TaqMan probe may be used, and optionally, an RNase P reference gene primer/probe set is used.

In step (b), single-plex or multiplex PCR amplification may be used.

In step (b), a second primer pair and a second TaqMan probe may be used.

In step (b), a third primer pair and a third TaqMan probe may be used.

In step (b), a fourth primer pair and a fourth TaqMan probe may be used.

In step (b), (Y1) a first primer pair and a first TaqMan probe and (Y2) a second primer pair and a second TaqMan probe may be used simultaneously or successively for PCR amplification.

In step (b), by comparing the Ct value, the copy number of the TCR transgene may be determined.

In step (b), the Ct value of the sample to be tested may be compared with a standard value or a standard curve to determine the copy number of the TCR transgene.

The sample to be tested may include a nucleic acid sample.

The nucleic acid sample may be the total nucleic acids extracted from M cells, where M is a positive integer. For example, M may be 1, 2, 3, 4, 5, 6, 7, 8, 9 or 10.

Step (b) may comprise the following steps:

S1) selecting a conserved region of mouse TCR gene as a target gene fragment;

S2) inserting the target gene fragment into a vector to construct a standard plasmid, using it as a standard stock solution, and then performing serial dilutions to obtain a series of standard products;

S3) performing real-time fluorescent quantitative PCR (qPCR) on the genes of the standard substances and the samples to be tested, drawing a standard curve based on the Ct values and copy number of the series of standard substances, and obtaining a calculation formula;

S4) bringing the Ct value of the sample to be tested into the calculation formula of the standard curve in step S3) to obtain the gene copy number of the sample to be tested.

Step (b) may comprise the following steps:

R1) selecting a conserved region of mouse TCR gene as a target gene fragment and a reference gene with a known sequence;

R2) inserting the target gene fragment into a vector to construct a standard plasmid, using it as a standard stock solution, and then performing serial dilutions to obtain a series of standard products;

R3) using the reagent according to claim 1, performing real-time fluorescent quantitative PCR (qPCR) on the genes of the standard substances and the samples to be tested, drawing a standard curve based on the Ct values and copy numbers of the series of standard substances, and obtaining a calculation formula;

R4) using the Ct value of a reference gene RNaseP to calculate the calibration factor for each sample;

R5) obtaining the copy number of the TCR gene per μg of the genome in the sample to be tested by comparing with the copy number of the reference gene per μg of the genome.

Step (b) may further comprise a step of adding human background DNA.

The human background DNA may be the genomic DNA of PBMC.

In one embodiment, the amount of the human background DNA is 50 ng.

In one embodiment, the primer concentration is 0.45 μM, and the probe concentration is 0.125 μM.

In one embodiment, the minimum number of copies of the standard substance is 10, or the minimum copy number point is 10 copies.

Main Advantages of the Present Disclosure:

1. The linear coefficient of determination ($R^2$) of the standard curves in the detection method provided by the present disclosure was in a range from 0.994 to 0.999. The amplification efficiency was 92.3% to 101.6%. The within-run precision of each concentration point in the standard curves was in a range from 0.09% to 1.55%. The between-run precision was in a range from 1.09% to 3.07%. The within-run precision of reference gene RNaseP was in a range from 0.58% to 2.30%, and the between-run precision was 1.18%. Therefore, the present disclosure has a good linear relationship, amplification efficiency and precision.

2. The primer/probe sets of the present disclosure provide a quick and reliable detection method for determining the copy number of a mouse TCR gene in T cells during clinical testing and product release.

3. The duplex reaction method in the present disclosure can achieve simultaneous detection of a target gene and a reference gene in a reaction, reducing the likelihood of an erroneous additional detection of the reference gene.

The present invention may be better understood by reference to the following non-limiting examples, which are presented in order to more fully illustrate the preferred embodiments of the invention. They should in no way be construed to limit the broad scope of the invention. The present disclosure will be further described in conjunction with specific embodiments. It should be understood that these embodiments are intended to describe the present disclosure only and not to limit the scope of the present disclosure. Unless specific conditions are indicated, the experimental methods in the following embodiments normally adopt conventional conditions, such as the conditions described in Sambrook et al., Molecular Cloning: Laboratory Manual (New York: Cold Spring Harbor Laboratory Press, 1989), or the conditions recommended by the manufacturer. Unless otherwise stated, percentages and parts are weight percentages and parts by weight.

Materials and General Methods

I. Experimental Materials

1. Instruments:

| Reagent name | Source | Goods No. | Use |
|---|---|---|---|
| QIAamp blood sample midi kit | Qiagen | 51185 | Extract cell or blood genomic DNA |
| Premix for Taqman gene identification | Thermo Fisher | 4304437 | Amplify the target gene |
| Customized probe for copy detection reaction | Thermo Fisher | 4400296 | Primer/probe of TCR sequence |
| RNase P probe for TaqMan copy reference reaction | Thermo Fisher | 4403328 | RNase P reference gene primer/probe |
| Human peripheral blood monocyte genome | | | Serve as a genomic background and a TCR gene negative control |
| Modified T cell genomic DNA | Extraction of C-TCR055 transduced T cells | From QC department | TCR gene positive control |
| pUC57-PC25J | Xitu | | Standard curve |
| Buffer solution for dilution of standard substance | Takara | 9160 | Dilute plasmids to generate standard curves |
| Buffer solution for re-suspension | Teknova | T0221 | For diluting the negative and positive controls |

-continued

| Instrument name | Model | Manufacturer | Instrument No. |
|---|---|---|---|
| Ultra-micro spectrophotometer | Nanodrop 2000 R737 | Thermo Fisher | SH7028 |
| Small desk centrifuge | D3024R | SCILOGEX | SH7056 |
| Flat centrifuge | 5804R | Eppendorf | SH7045 |
| Real-time fluorescence quantitative PCR instrument | Quant Studio Dx | Thermo Fisher | SH0491 |

2. Primers and Probes Information:

2.1 Design of Primer Probes:

Four pairs of primer probes were designed according to the sequence of the conserved regions of the mouse TCR gene, as shown in FIG. 1.

2.2 Sequences of Primer Probes Information:

The primers and probes were ordered from Thermo Fisher.

| | 5' to 3' sequence | SEQ ID No.: |
|---|---|---|
| A1 (MouseCb2_CDCE39P) | | |
| Forward primer | CGAGATCGCCAACAAGAGGAA | 4 |
| Reverse primer | TGCACCTCCTTGCCATTCA | 5 |
| Probe | 6 FAM-CCCACCAGGACAGCT CC-MGB | 6 |
| B1 (MouseCa_CD9HJA2) | | |
| Forward primer | TGCCTGTTCACCGACTTTGAT AG | 7 |
| Reverse primer | CACGGTCTTGTCTGTGATAAA GGT | 8 |
| Probe | 6 FAM-CAGATCAATGTGCCT AAGACAATG-MGB | 9 |
| C1 (MouseCa_CDAAANT) | | |
| Forward primer | TGCCACCCTGACAGAGAAGA | 10 |
| Reverse primer | GCCCATCACGGACAGGTT | 11 |
| Probe | 6 FAM-ACAGACATGAACCTG AATTTT-MGB | 12 |
| D1 (MouseCb2_CDDJXUM) | | |
| Forward primer | GGGAAGGGCAGACTGTGG | 1 |
| Reverse primer | GCAGGATCTCGTACAGGATTG TG | 2 |
| Probe | 6 FAM-CATCACCAGCGCCTC CTATCA-MGB | 3 |

3. Plasmid Synthesis and Packaging 3.1 Design, Synthesis and Packaging of a Standard Plasmid (pUC57-PC25J)

The standard plasmid is designed according to the target fragment detected by the TaqMan primer probe. Specifically, the two conserved regions of the mouse TCR gene are constructed on a pUC57 vector. The sequence of the conserved region of the mouse TCR gene is as follows:

(SEQ ID No.: 13)

gacctgcgcaatgtgacccccctaaggtgtccctgttcgagccttctaa ggccgagatcgccaacaagaggaaggccaccctggtgtgcctggcaaggg gcttctttccagatcacgtggagctgtcctggtgggtgaatggcaaggag gtgcactctggcgtgagcacagacccccaggcctacaaggagtccaacta ttcttactgcctgtctagccggctgagagtgagcgccacctttggcaca accccaggaatcacttccgctgtcaggtgcagtttcacggcctgtccgag gaggataagtggcctgagggctctcccaagcctgtgacacagaacatcag cgccgaggcatggggaagggcagactgtggcatcaccagcgcctcctatc agcagggcgtgctgagcgccacaatcctgtacgagatcctgctgggcaag gccaccctgtatgctgtgctggtgtcaactctggtggtcatggctatggt gaaacggaaaaactccatccagaatccagagcccgccgtgtatcagctga aggacccacggagccaggatagcaccctgtgcctgttcaccgactttgat agccagatcaatgtgcctaagacaatggagtccggcacctttatcacaga caagaccgtgctggatatgaaggccatggacagcaagtccaacggcgcca tcgcctggtctaatcagacaagcttcacctgccaggatatctttaaggag acaaacgccacctacccatctagcgacgtgccctgtgatgccaccctgac agagaagagcttcgagacagacatgaacctgaattttcagaacctgtccg tgatgggcctgagaatcctgctgctgaaggtggccggcttcaatctgctg atgacactgcgcctgtggtcctct 3.2 pUC57 Empty Plasmid pUC57 is an empty plasmid not containing the target gene.

4. Negative Control

The negative control (NC) is the genomic DNA of human PBMC.

5. Positive Control

The positive control (PC) comes from the genomic DNA of TCR-positive cells.

| | | $10^9$ | $10^8$ | $10^7$ | $10^6$ |
|---|---|---|---|---|---|
| Concentration of the prepared plasmid solution (copies/μL) | | $10^9$ | $10^8$ | $10^7$ | $10^6$ |
| Dilution process | Add Easy Dilution/μL | 90 | 90 | 90 | 90 |
| | Concentration of the added plasmid solution copies/μL | $10^{10}$ | $10^9$ | $10^8$ | $10^7$ |
| | Volume of the added plasmid solution/μL | 10 | 10 | 10 | 10 |

6. Single-Plex Reaction Experiment:

Concentrations of standard primer probes (TCR primer 0.9 μM, probe 0.25 μM)

| Reagent | Volume |
|---|---|
| 2× TaqMan Master Mix | 10 μL |
| 20× reference primer/probe mix | 0 μL |
| 20× customized primer/probe mix | 1 μL |
| DNA sample (without a gDNA background) | 5 μL |
| Nuclease-Free H₂O | 4 μL |
| Total volume | 20 μL |

7. Duplex Reaction Experiment:

Concentrations of standard primer probes (TCR primer 0.9 μM, probe 0.25 μM)

| Reagent | Volume |
|---|---|
| 2× TaqMan Master Mix | 10 μL |
| 20× reference primer/probe mix | 1 μL |
| 20× customized primer/probe mix | 1 μL |
| DNA sample | 5 μL |
| Nuclease-Free H$_2$O | 3 μL |
| Total volume | 20 μL |

Duplex primer probe concentrations (TCR primer 1.8 μM, probe 0.5 μM)

| Reagent | Volume |
|---|---|
| 2× TaqMan Master Mix | 10 μL |
| 20× reference primer/probe mix | 1 μL |
| 20× customized primer/probe mix | 2 μL |
| DNA sample | 5 μL |
| Nuclease-Free H$_2$O | 2 μL |
| Total volume | 20 μL |

Low primer probe concentrations (TCR primer 0.45 μM, probe 0.125 μM)

| Reagent | Volume |
|---|---|
| 2× TaqMan Master Mix | 10 μL |
| 20× reference primer/probe mix | 1 μL |
| 20× customized primer/probe mix | 0.5 μL |
| DNA sample | 5 μL |
| Nuclease-Free H$_2$O | 3.5 μL |
| Total volume | 20 μL | qPCR detection was conducted in the machine. The reaction was carried out under standard conditions:

Polymerase activation: 10 min at 95° C.

PCR: 40 cycles

Denaturation: 15 sec at 95° C.

Anneal/Extend: 60 sec at 60° C.

8. Processing of Experimental Results:

After the end of the reaction, the software automatically output the Ct value of each sample and the TCR gene copy numbers of the negative and positive controls of each reaction. Based on the Ct value of the RNaseP gene, the calibration factor (CF) of each sample was calculated as follows: $CF1=2^{-(CtRNaseP\ (NC)-CtRNaseP(PC))}$. $CF2=Ct(PC)/$ Average Ct(PC), where Average Ct(PC) is the average value of the Ct values of the positive control in the previous error-free determinations. The TCR gene copy number in 1 μg of PC genome was calculated as follows:

TCR gene copy number=Copy number/amount of DNA added in each reaction (ng)×CF1×CF2× 1000 ng

9. Data Analysis:

The $R^2$ of standard curves should be 0.99, with the amplification efficiency ranging from 90% to 110%. The Ct threshold of the TCR gene detection is 0.1, which facilitates comparison between groups during the optimization of the experimental protocol. The threshold can be set to be "Auto" during actual tests. The Ct threshold for detection of the RNaseP reference gene is set to be an automatic threshold. The Ct values of NTC and NC controls should be none or ≥39.

Example 1 Single-Plex TaqMan qPCR

In this experiment, the amplification results of four sets of primer-probe reagents with and without a DNA background were tested.

The method is as follows. In the presence of the TCR primers/probes and the absence of the reference gene RNaseP primers/probe, the standard curve parameters of four sets of TCR primers/probes without or with human background gDNA were tested.

The standard curves of the four sets of primer probes are as shown in FIGS. 2-1A to 2-1D and 2-2A to 2-2D, where the square symbols stand for a standard sample, the circle symbols a test sample.

The single-plex reaction parameters of four sets of primers/probes without background gDNA are as follows:

| Primer/probe name | Primers (μM) | Probe (μM) | Threshold | Efficiency | $R^2$ | 10 copies | $10^7$ copies |
|---|---|---|---|---|---|---|---|
| A1 | 0.9 | 0.25 | 0.1 | 100.538% | 0.994 | 35.735 | 16.443 |
| B1 | 0.9 | 0.25 | 0.1 | 97.952% | 0.998 | 35.163 | 15.272 |
| C1 | 0.9 | 0.25 | 0.1 | 93.171% | 0.998 | 38.317 | 17.183 |
| D1 | 0.9 | 0.25 | 0.1 | 97.686% | 0.998 | 36.222 | 16.068 |

The single-plex reaction parameters of four sets of primer probes with background gDNA are as follows:

| Primer/probe name | Primers (μM) | Probe (μM) | Threshold | Efficiency | $R^2$ | 10 copies | $10^7$ copies |
|---|---|---|---|---|---|---|---|
| A1 | 0.9 | 0.25 | 0.1 | 100.589% | 0.998 | 35.082 | 15.452 |
| B1 | 0.9 | 0.25 | 0.1 | 95.611% | 0.997 | 37.783 | 16.512 |
| C1 | 0.9 | 0.25 | 0.1 | 96.897% | 0.999 | 37.011 | 16.316 |
| D1 | 0.9 | 0.25 | 0.1 | 98.768% | 0.998 | 36.302 | 16.342 |

The Results Indicate that:

(a) The $R^2$ and amplification efficiency of the four sets of primers/probes were up to standard in the single-plex reaction in the presence or absence of the background human gDNA.

(b) In the presence of the background human gDNA, A1 and D1 showed higher amplification efficiency, higher sensitivity and excellent reliability in the single-plex reaction test.

(c) In the range from a minimum of 10 copies to a maximum of $10^7$ copies, in the presence or absence of background human gDNA, the four sets of primers/probes all could effectively amplify the required products. Specifically, A1 and D1 showed better amplification specificity and were almost free from interference of the background human gDNA, while the background human gDNA interfered with B1.

Example 2 Duplex TaqMan qPCR

In the presence of TCR primers/probe and a reference gene RNaseP primers/probe, the standard curve parameters of four sets of TCR primers/probe were measured in the presence of human background gDNA.

In the duplex reaction, in addition to the human monocyte genomic DNA simulating a patient's blood sample, the primers/probe for detecting the reference gene RNaseP were also added to the reaction system. While detecting the target TCR gene, the reference gene RNaseP was also detected. The results indicate that when a human gDNA simulation background was added to the duplex reaction, the $R^2$ and amplification efficiency of the four sets of primers were significantly reduced and were not up to standard. Relative to the other three sets of primers/probe, the D1 primer set generated better data in the duplex reaction which were close to the standard. The experimental conditions for primer D1 were optimized subsequently.

The standard curves of the four sets of primers/probe are shown in FIGS. 3A-3D, where the squares stand for a standard sample, the circles a test sample.

The duplex reaction parameters of four sets of primers/probe with background gDNA are as follows:

| Primer/probe name | Primers (μM) | Probe (μM) | Threshold | Efficiency | $R^2$ | 10 copies | $10^7$ copies |
|---|---|---|---|---|---|---|---|
| A1 | 0.9 | 0.25 | 0.1 | 80.733% | 0.986 | UND | 15.501 |
| B1 | 0.9 | 0.25 | 0.1 | 81.331% | 0.990 | 39.372 | 15.524 |
| C1 | 0.9 | 0.25 | 0.1 | 74.155% | 0.976 | UND | 16.519 |
| D1 | 0.9 | 0.25 | 0.1 | 87.745% | 0.993 | 39.223 | 16.225 |

Note:
UND = no signal value detected.

Example 3 Selection of the Lowest Copy Points of the Standard Curves

Figures 1, 4:
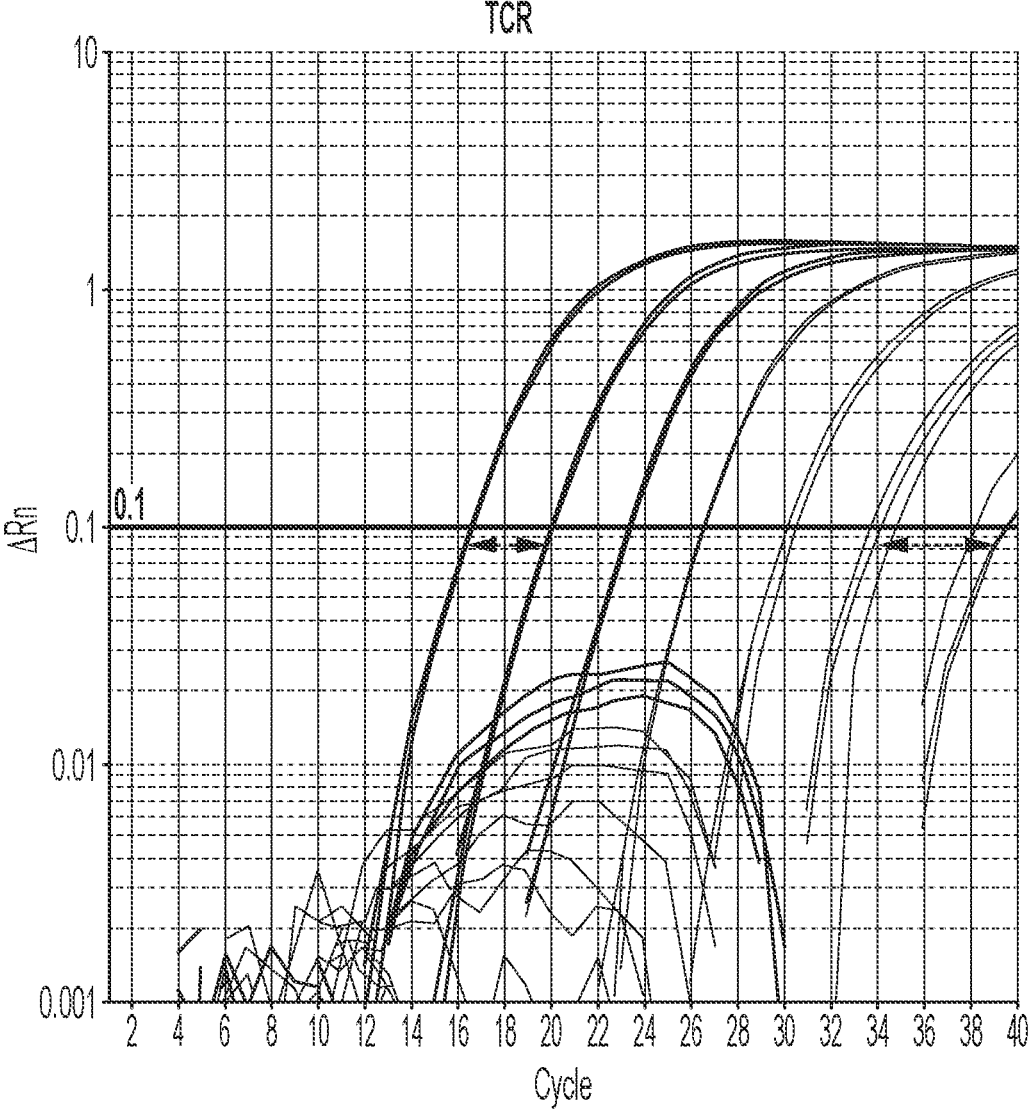
Figures 2, 4:
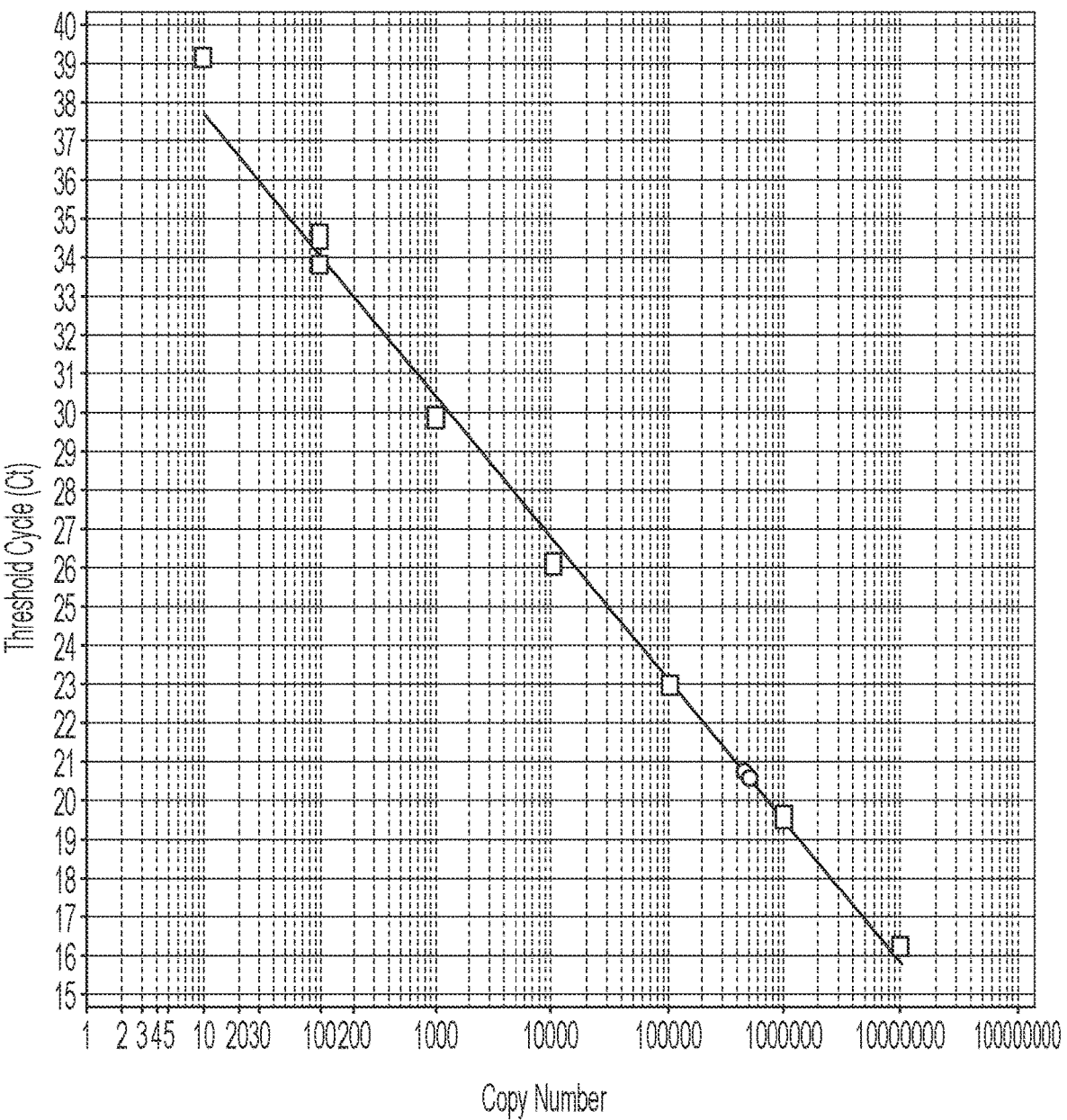

The above experimental results indicated that the error during reaction at low copy numbers of the standard curve is relatively large, as shown by the lengths of the two arrows in FIG. 4-1. Theoretically, the lengths of the two arrows should be equal. However, in the low copy number realm, the amplification efficiency is reduced significantly. Thus, increasing the minimum copy number was considered.

Figures 1A, 2:
FIGS. 2-1A, 2-1B, 2-1C, 2-1D, 2-2A, 2-2B, 2-2C and 2-2D show the standard curves of the four sets of primers/probes in single-plex reactions.
Figures 1B, 2:
Figures 1C, 2:
Figures 1D, 2:
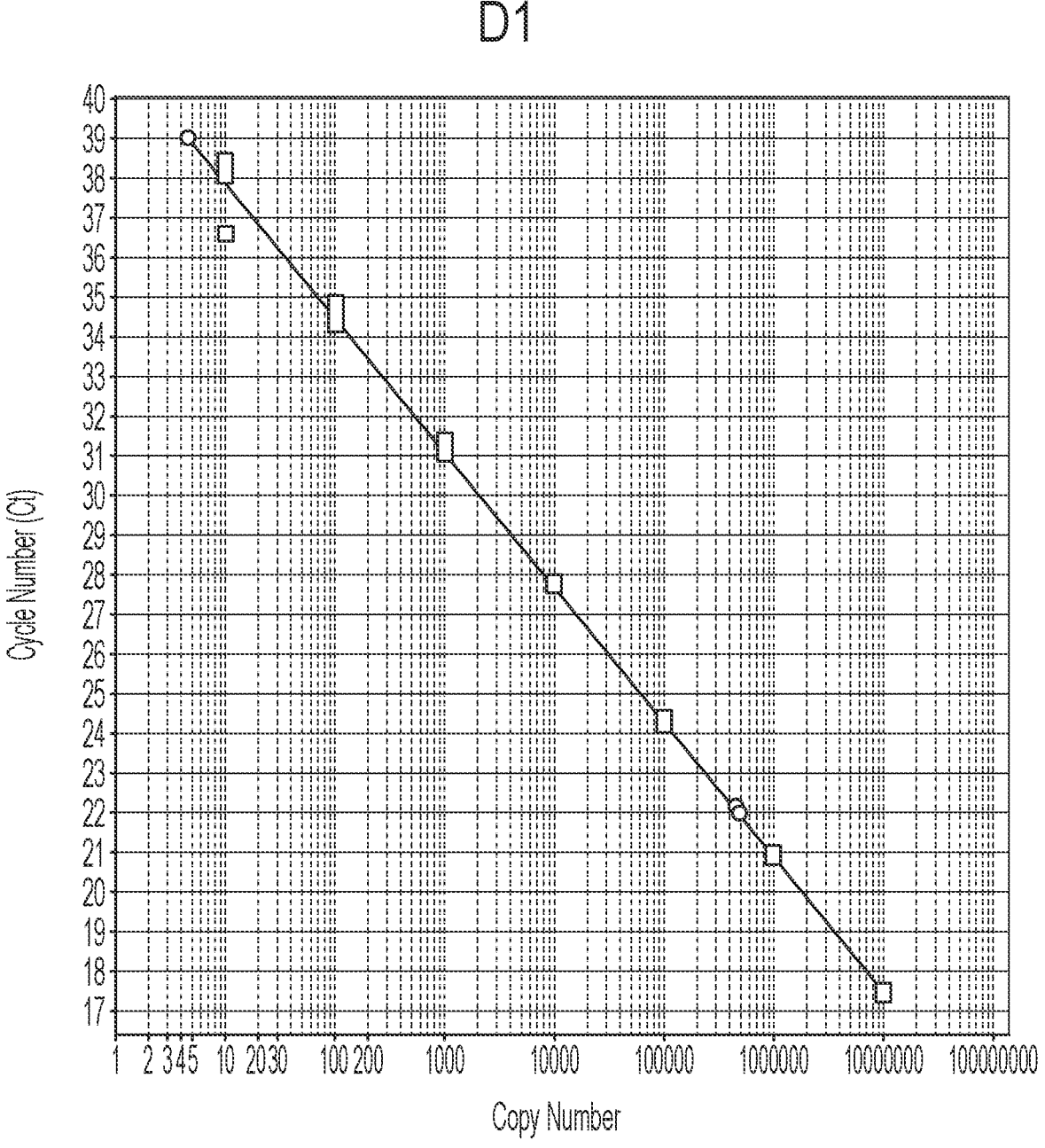
Figures 2, 2A:
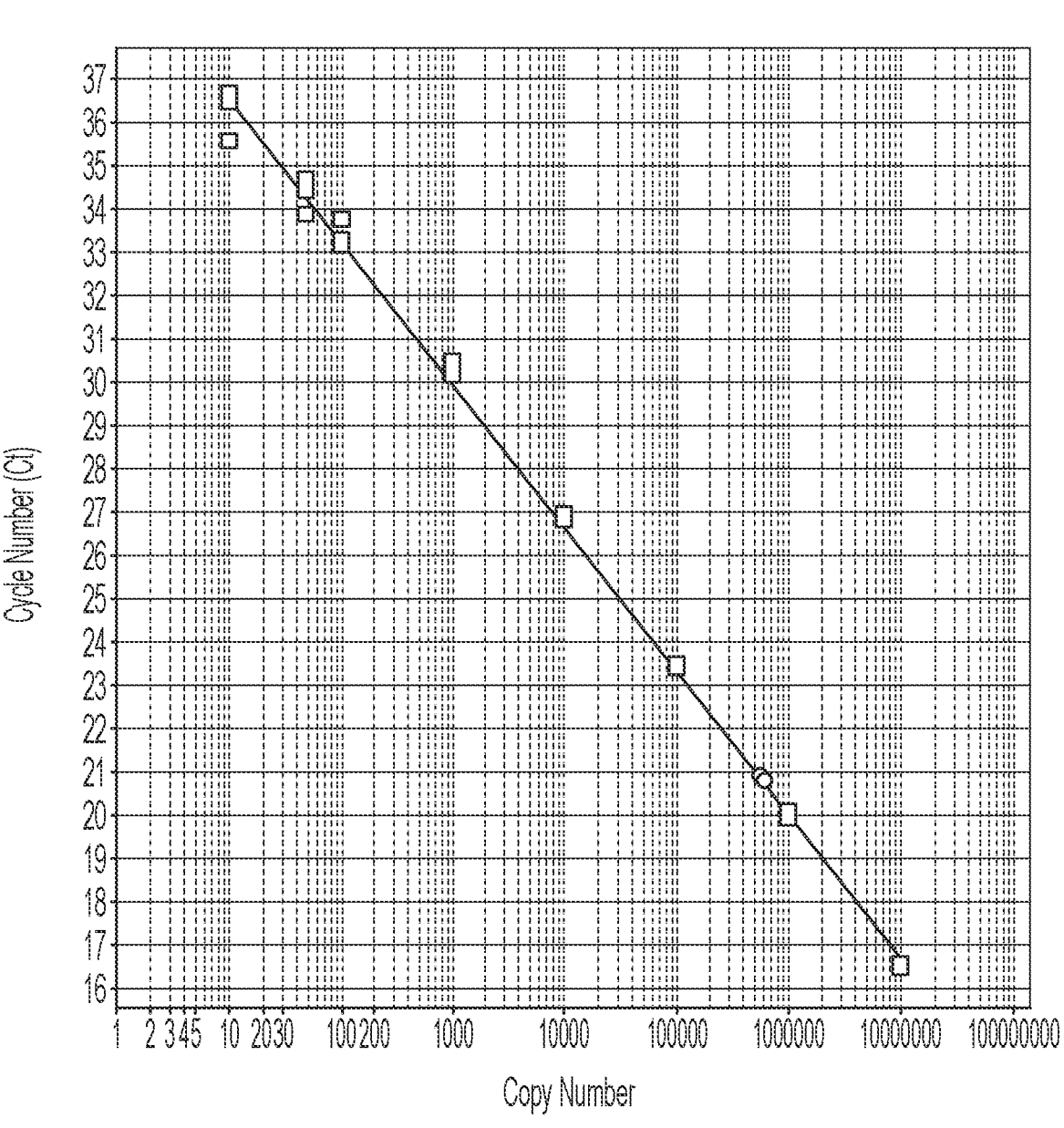
Figures 2, 2B:
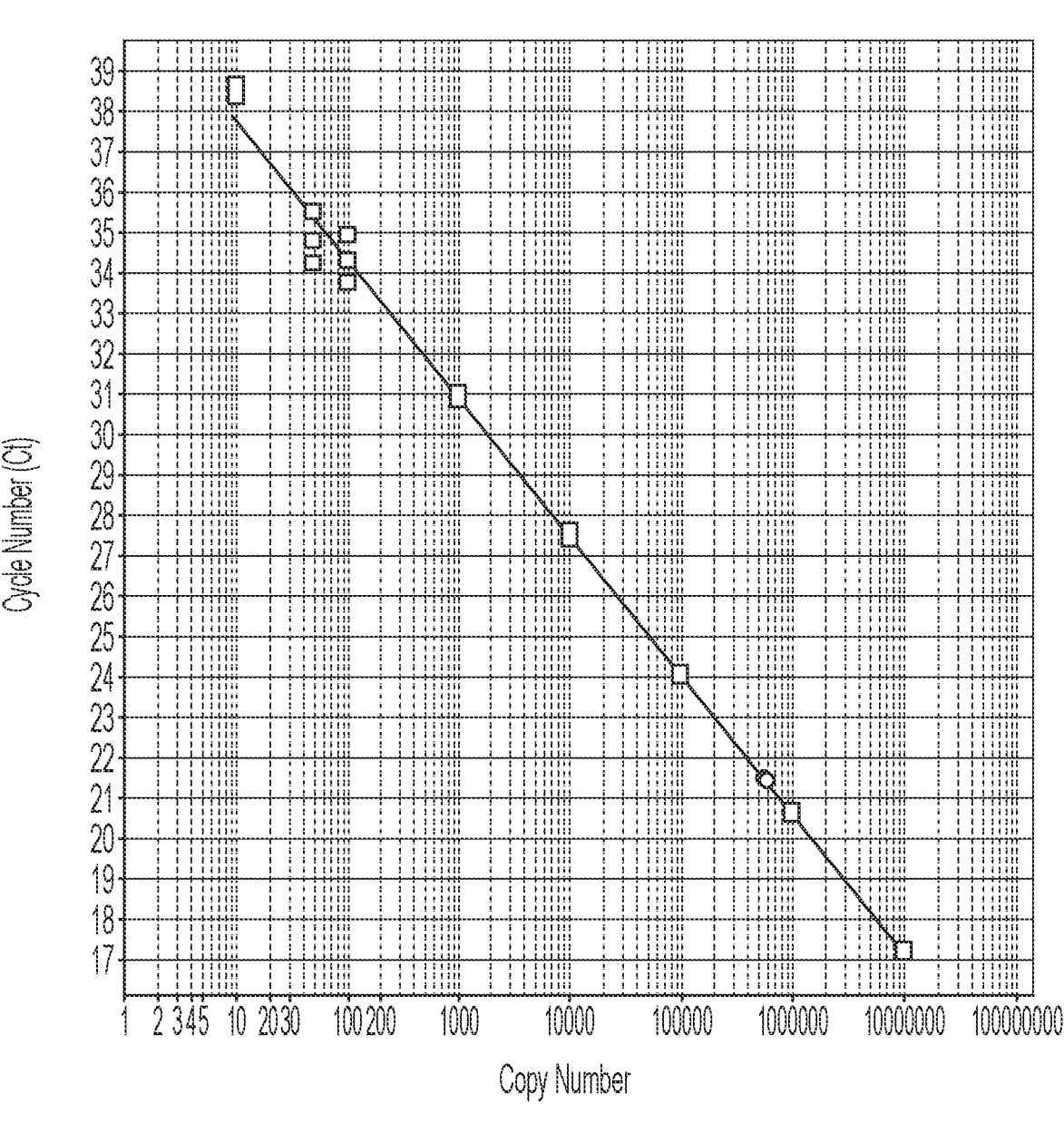
Figures 2, 2C:
Figures 2, 2D:
Figure 3A:
FIGS. 3A-3D show the standard curves of the four sets of primers/probes in duplex reactions.
Figure 3B:
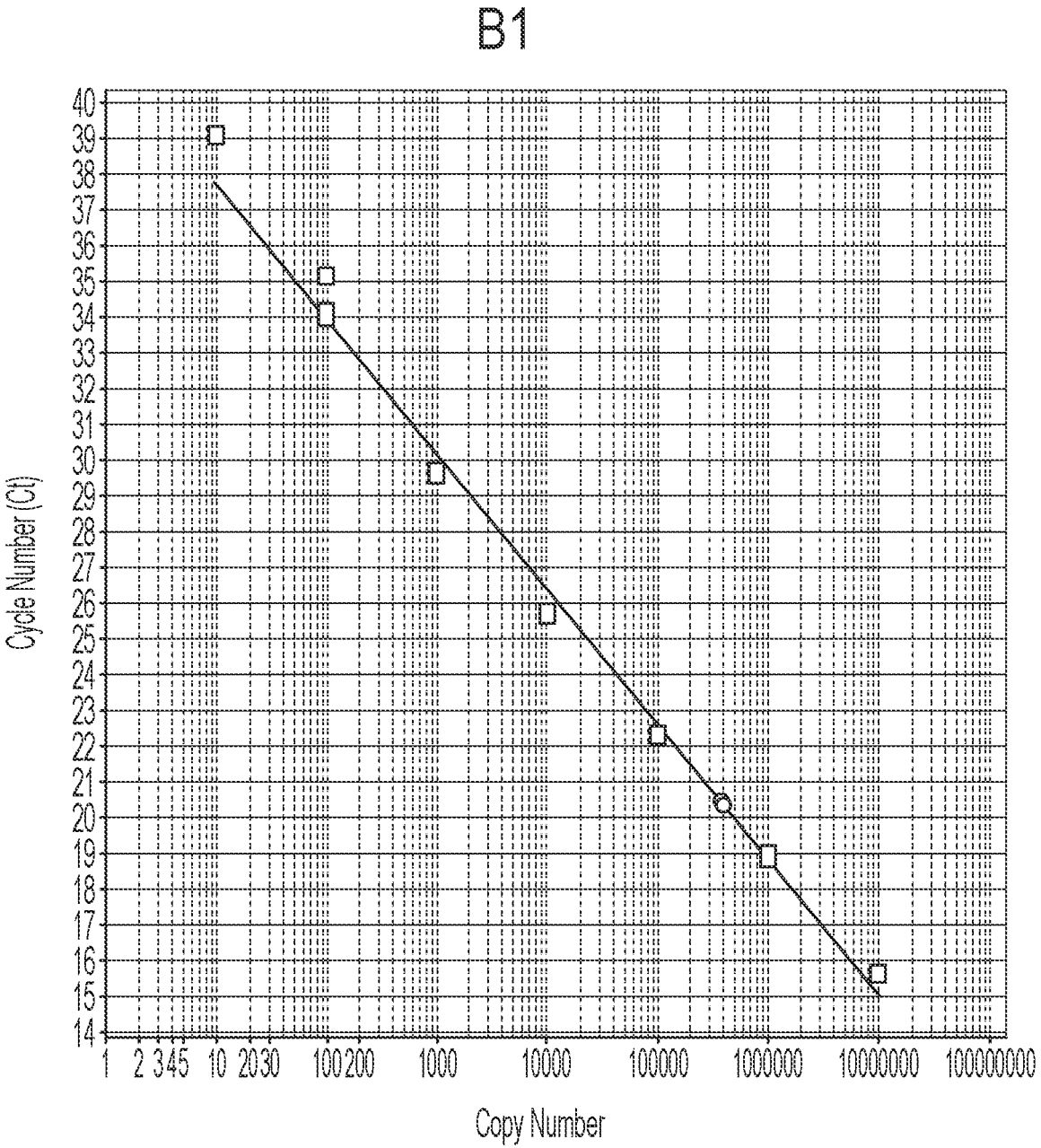
Figure 3C:
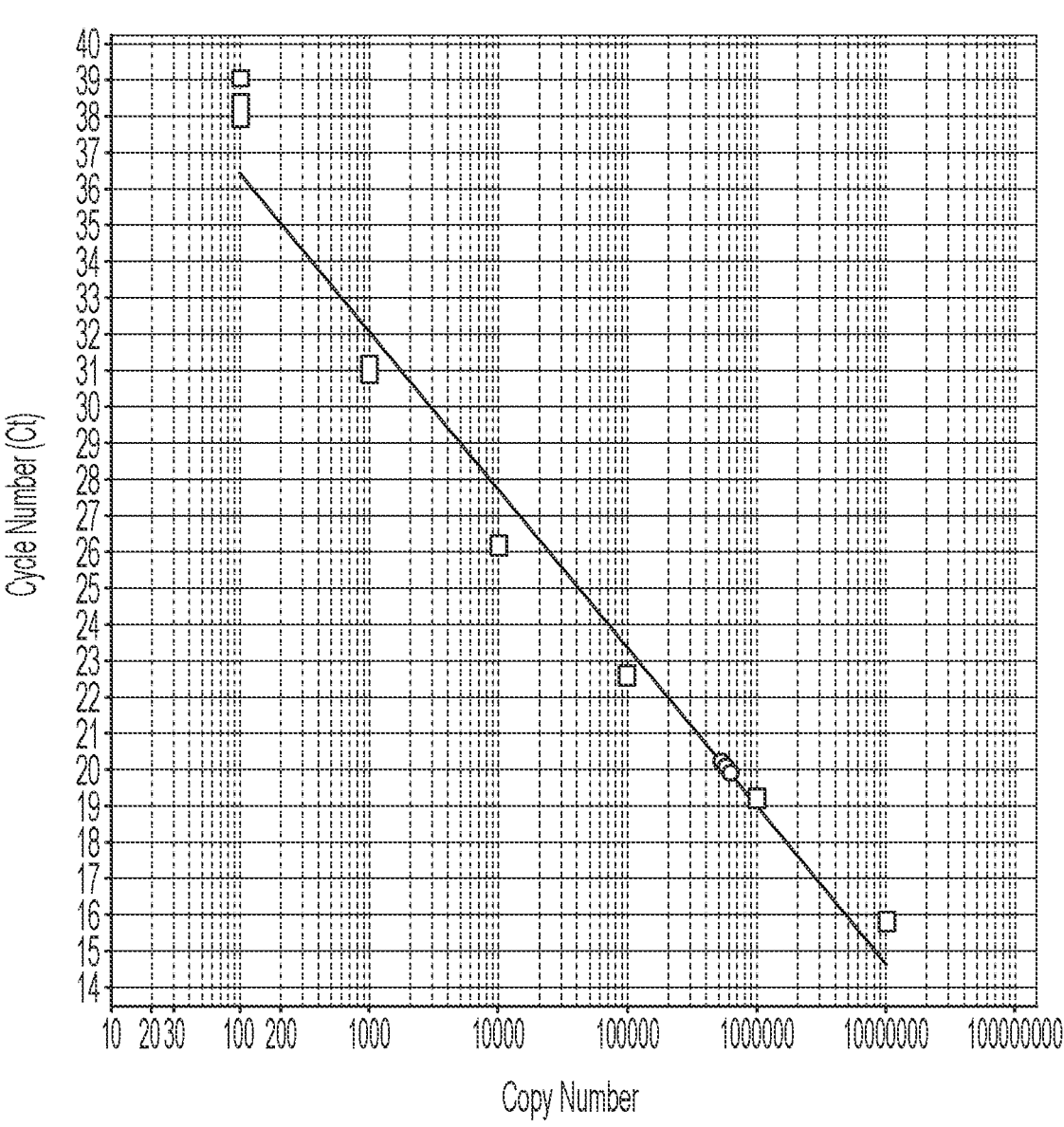
Figure 3D:
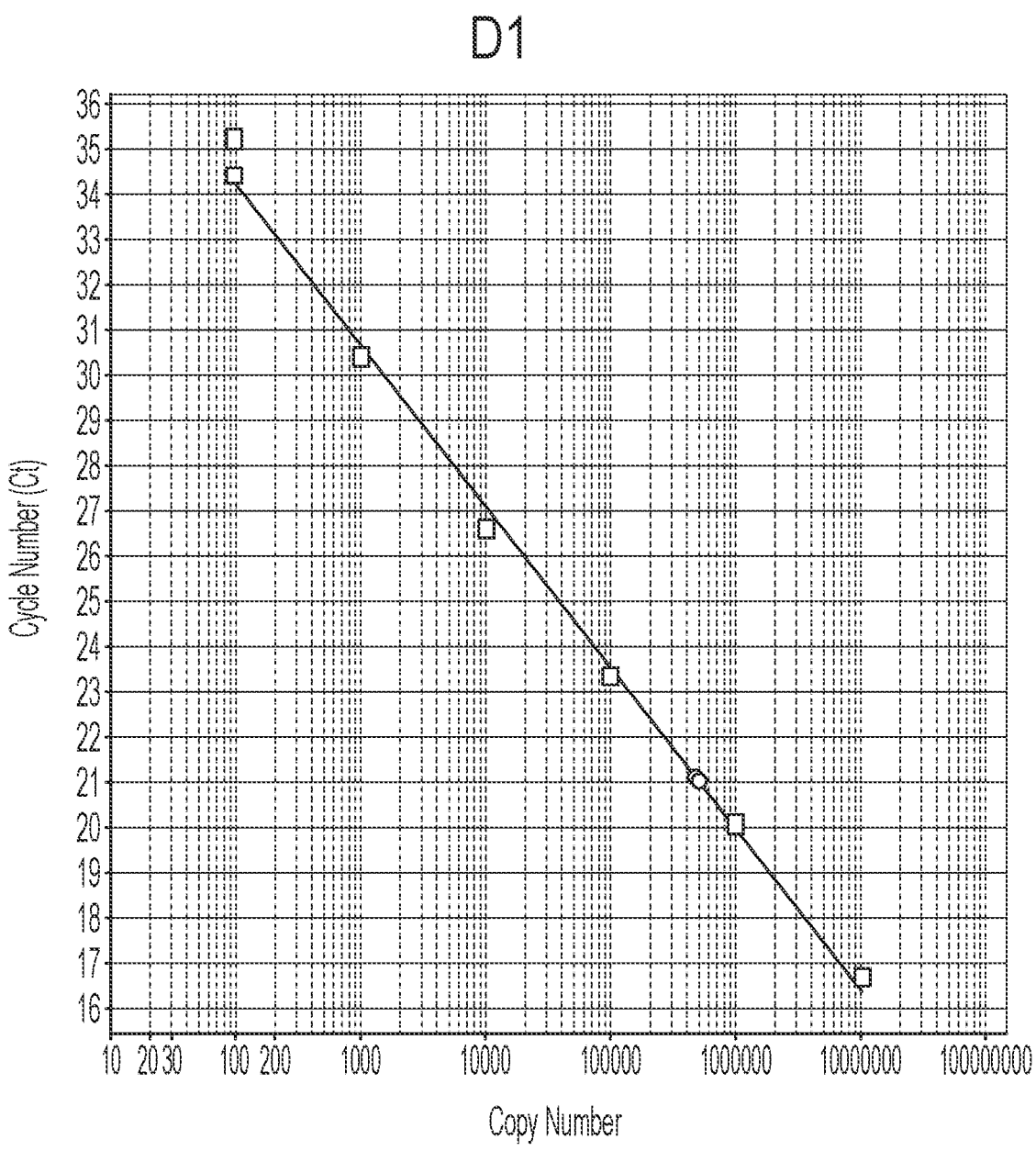
Figures 3, 4:
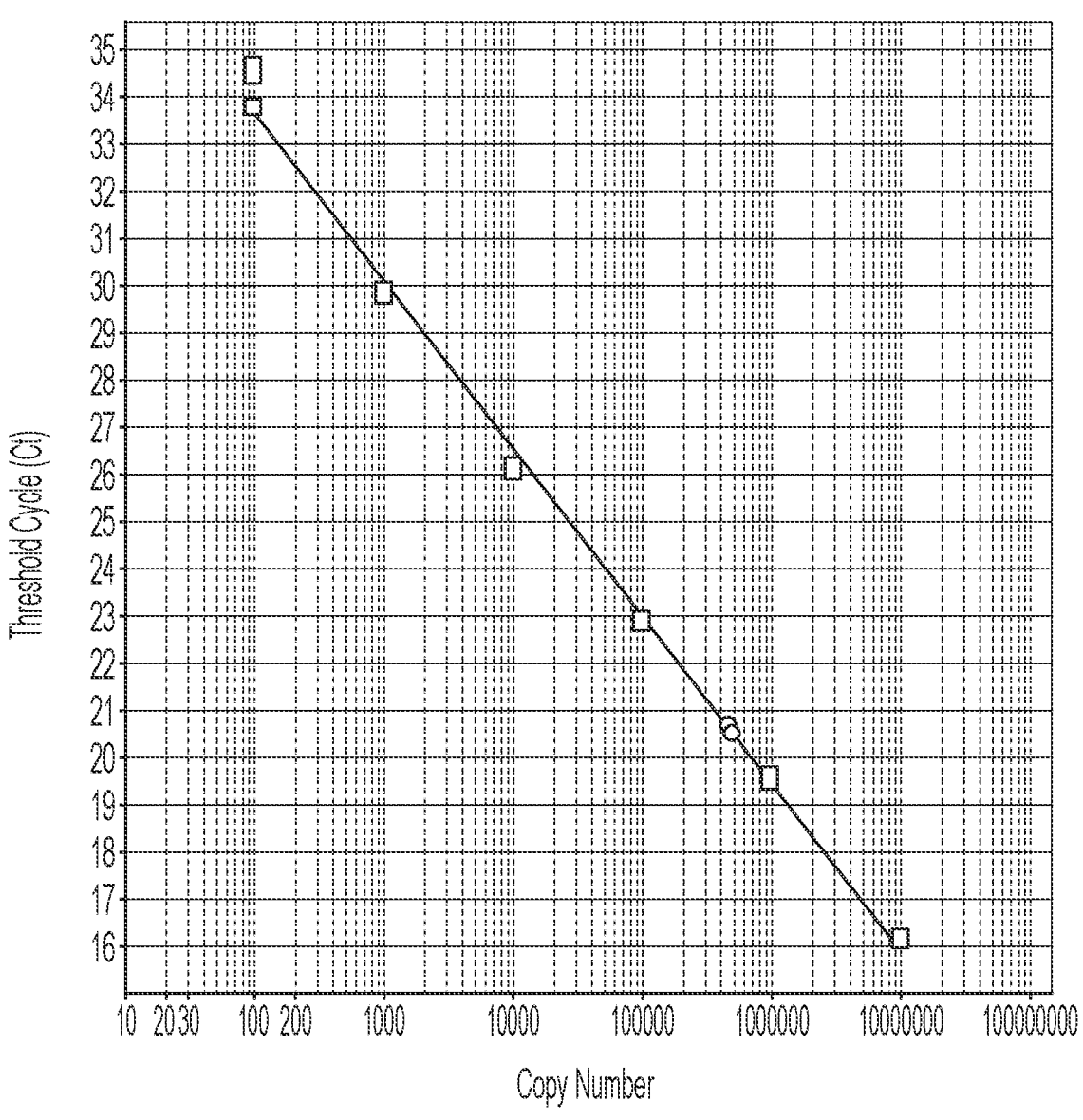
Figures 1, 5:
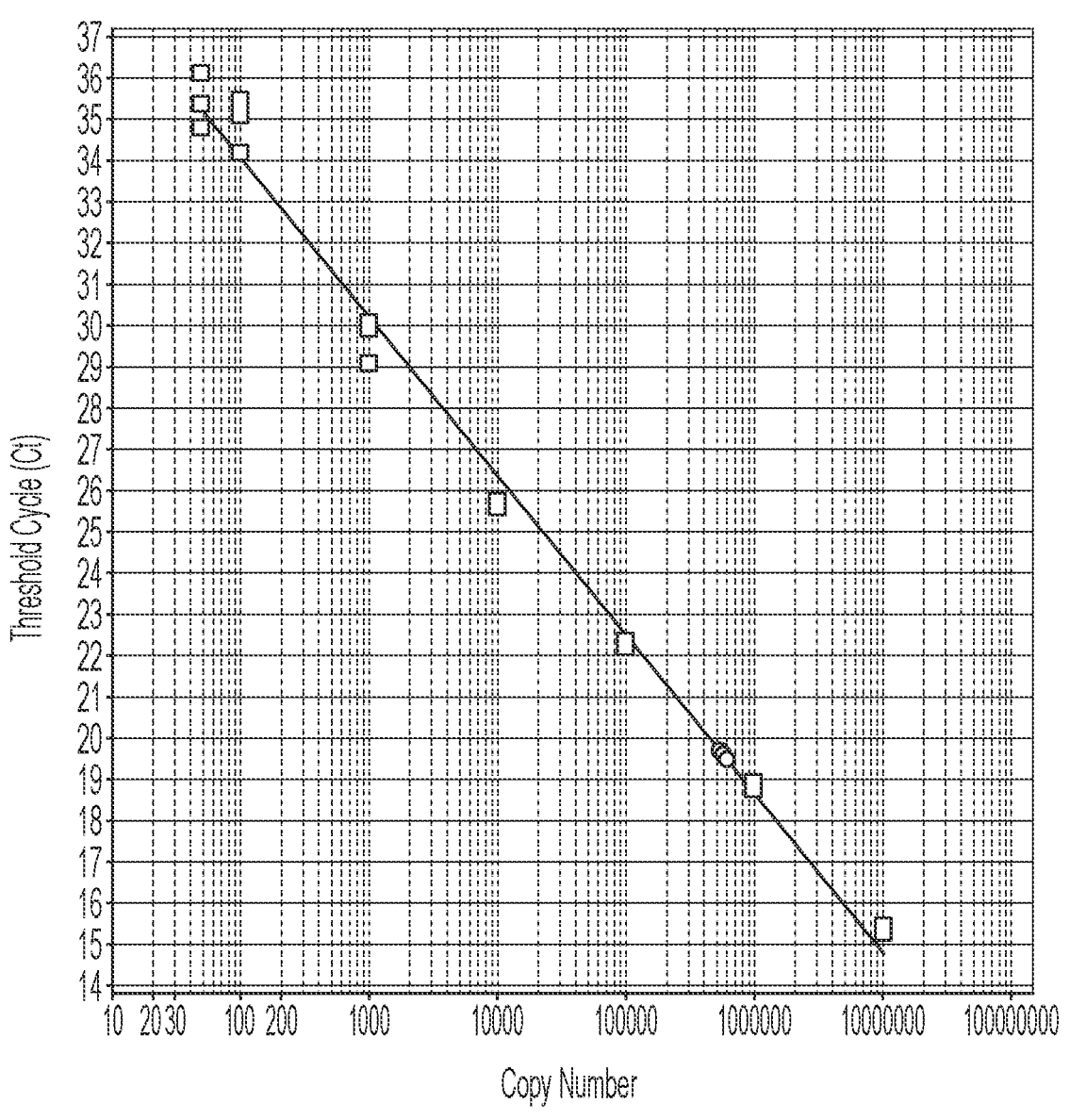
Figures 2, 5:
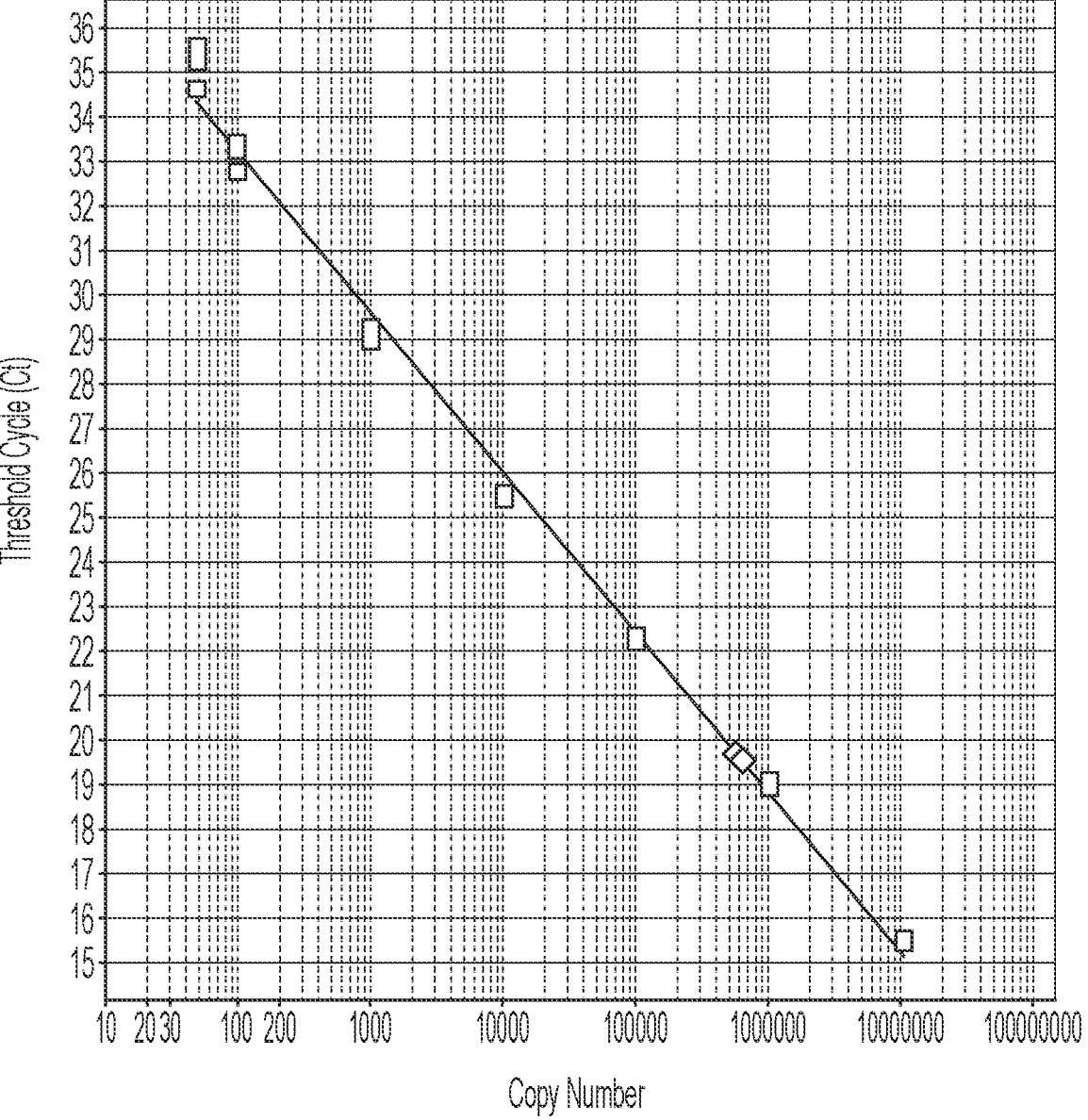
Figures 3, 5:
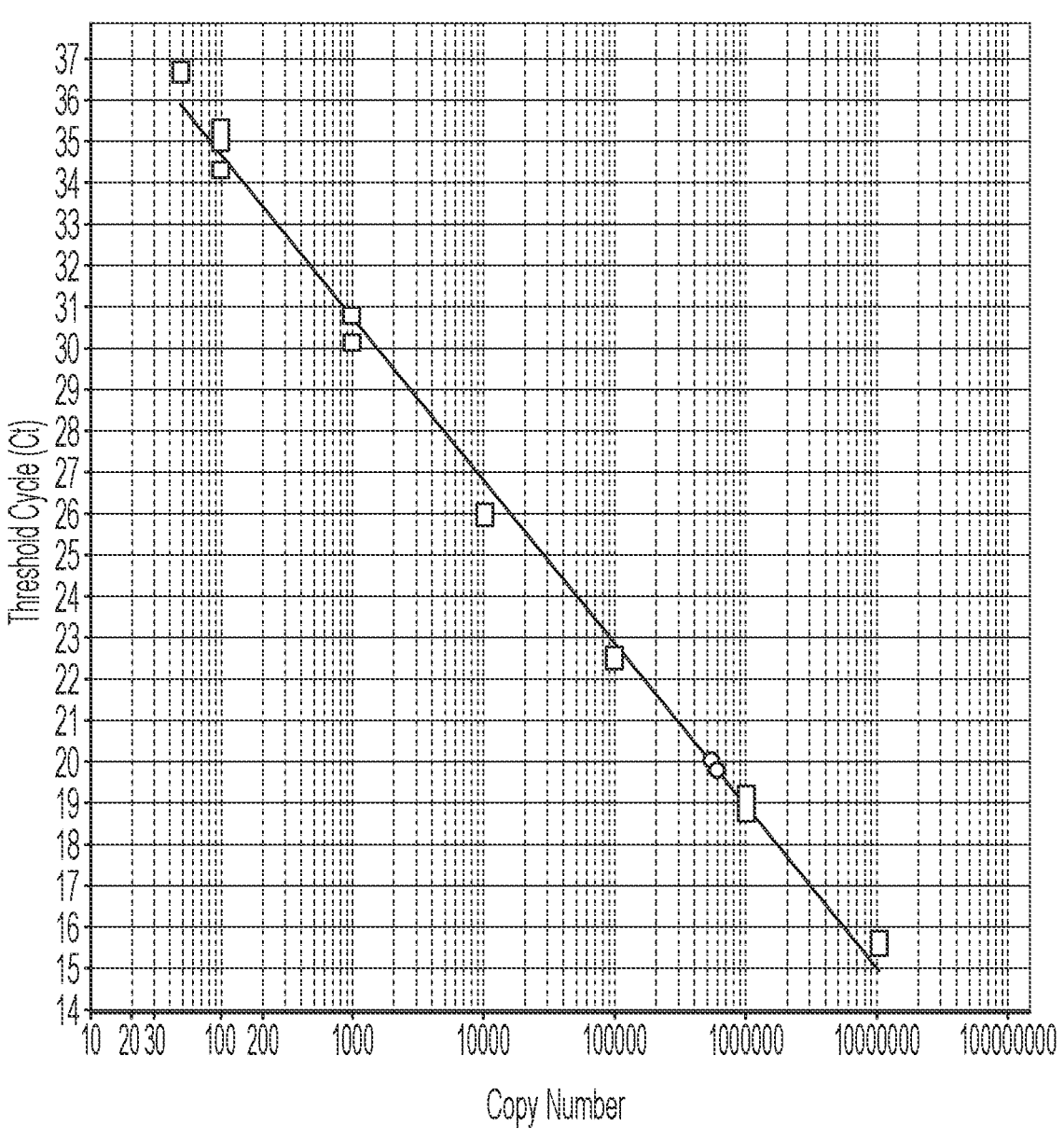
Figures 1, 6:
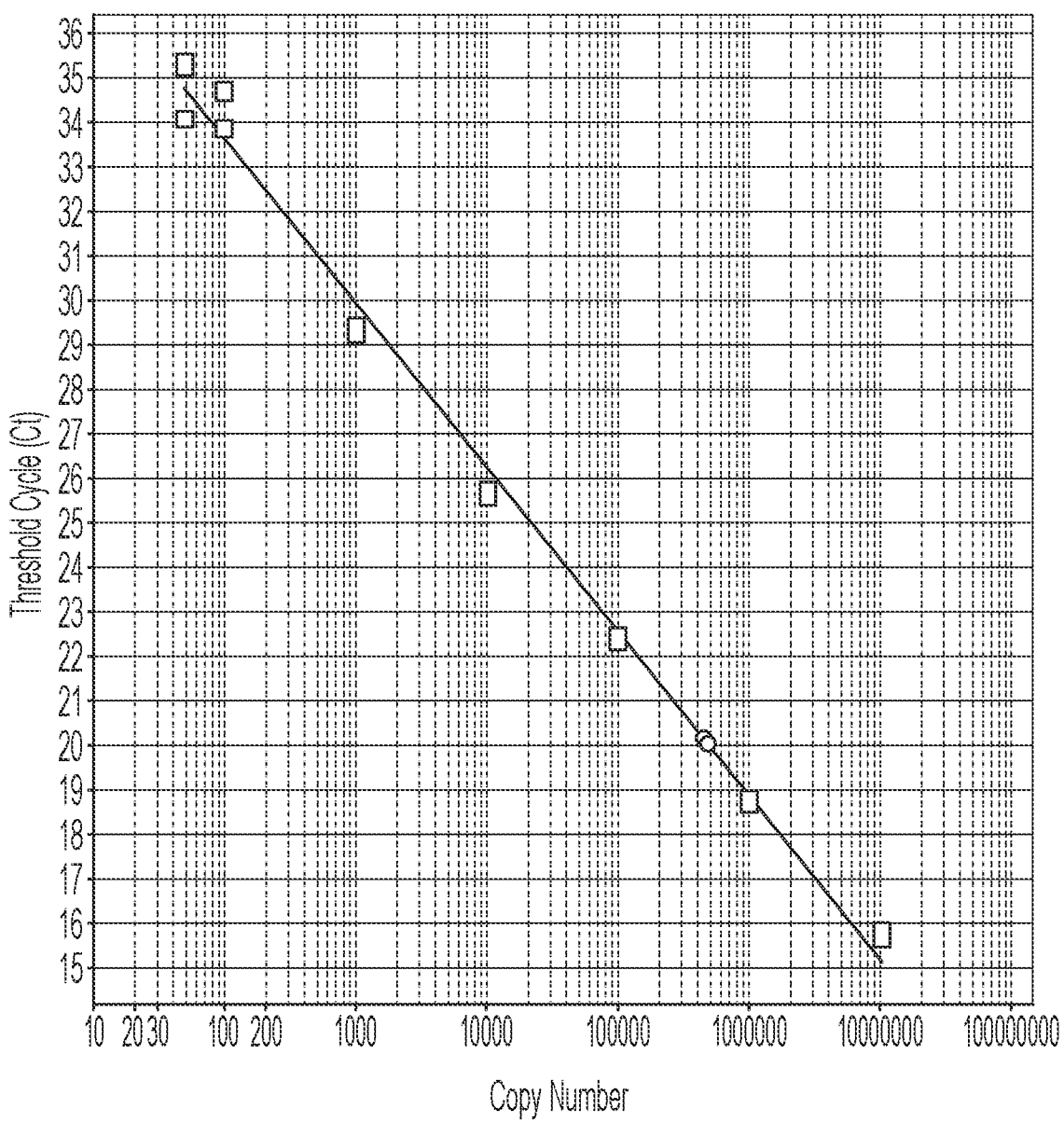
Figures 2, 6:
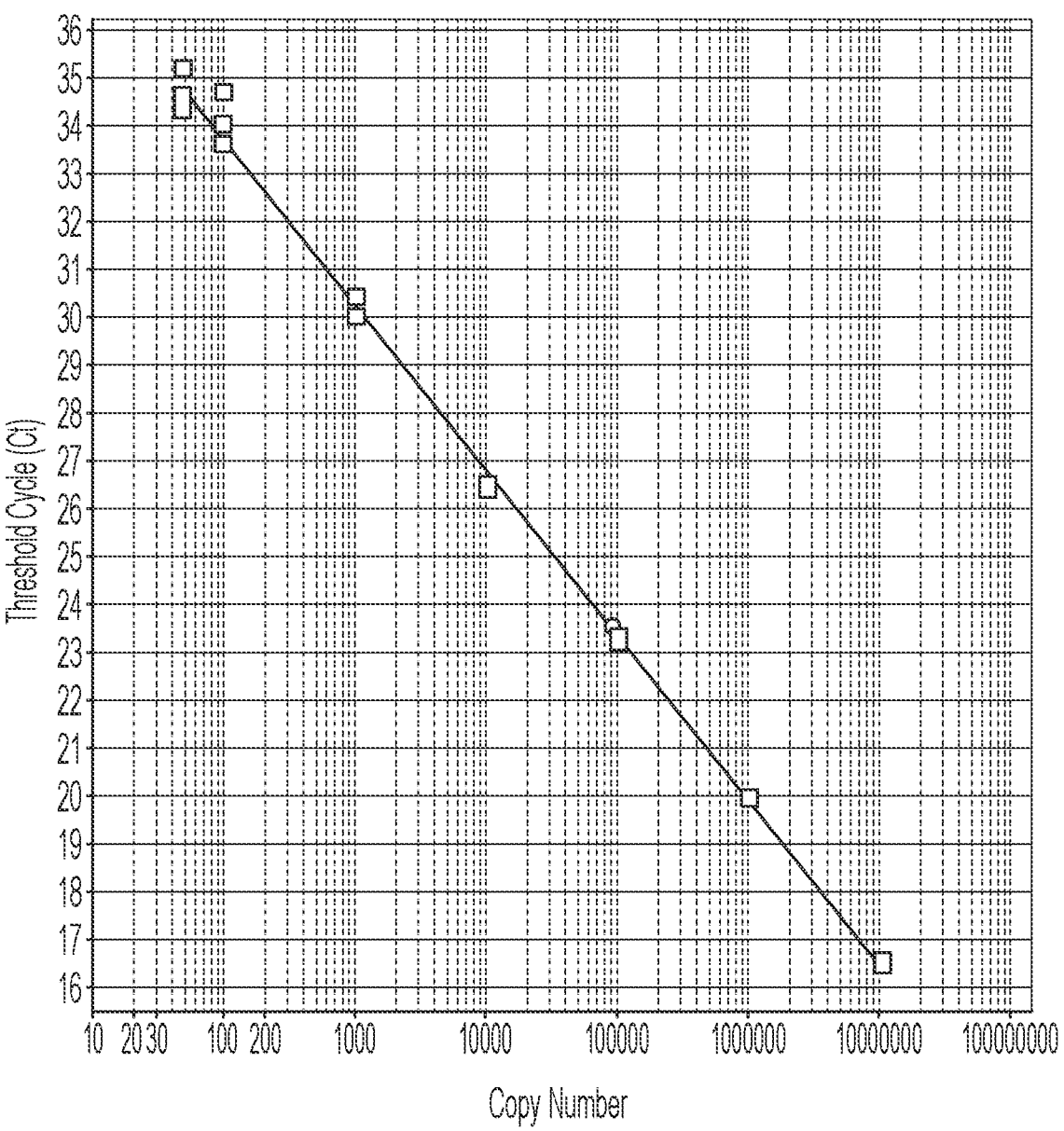
Figures 3, 6:
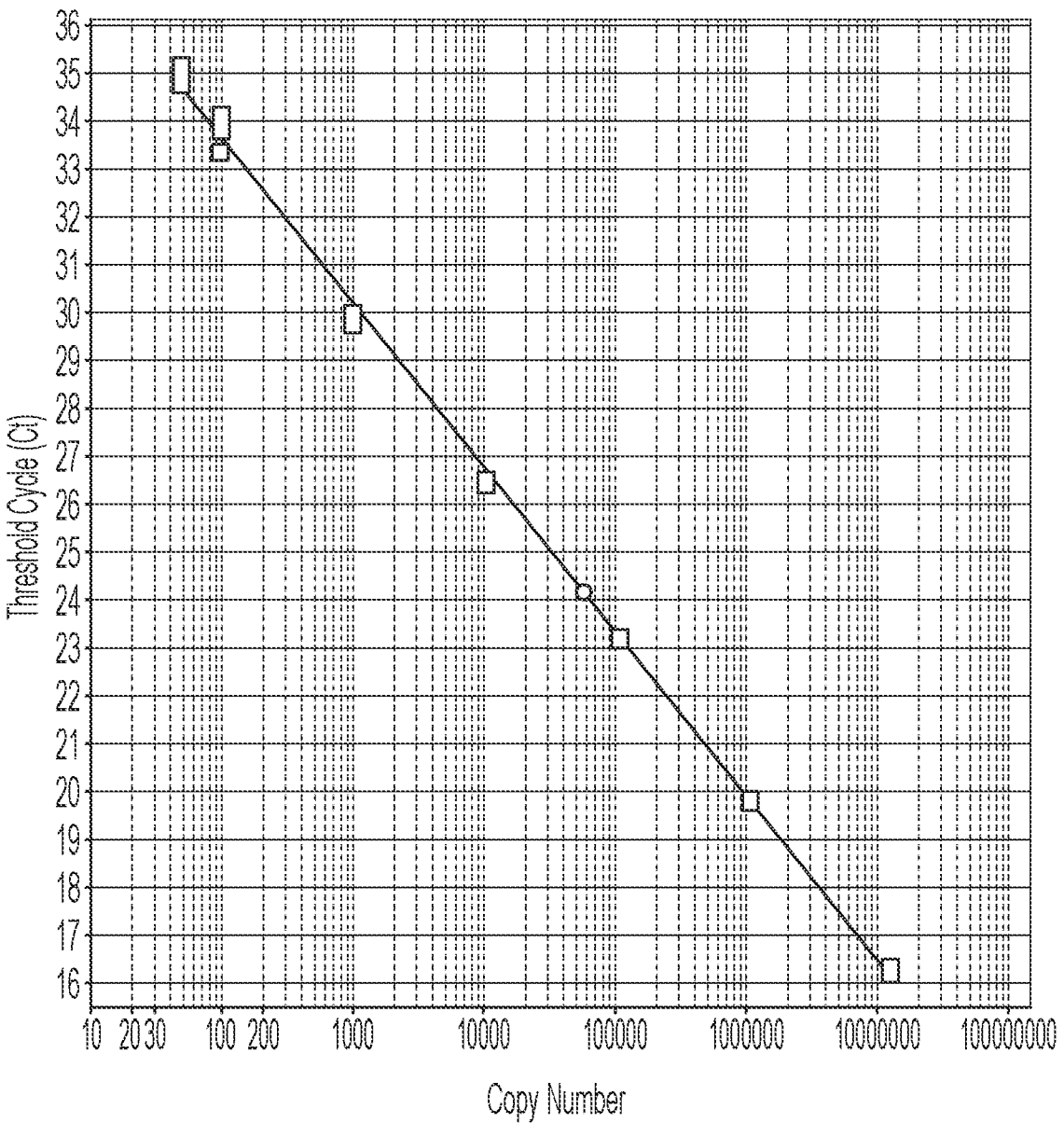
Figure 7A:
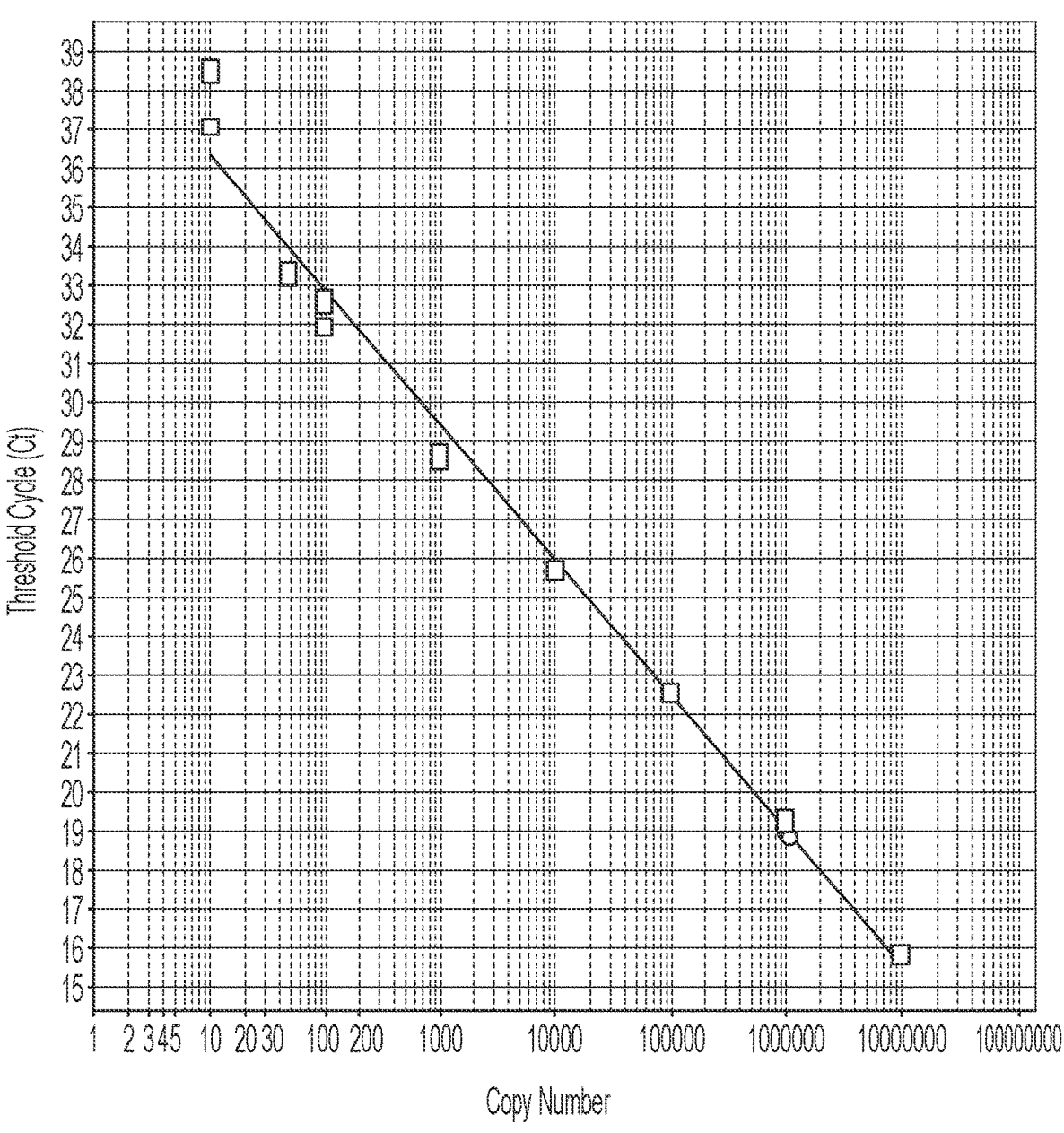
FIGS. 7A-7D show multiple repeated duplex-reaction tests for the D1 primers/probe with 0.45 $\mu$M primers, 0.125 $\mu$M probe under a background of 50 ng.
Figure 7B:
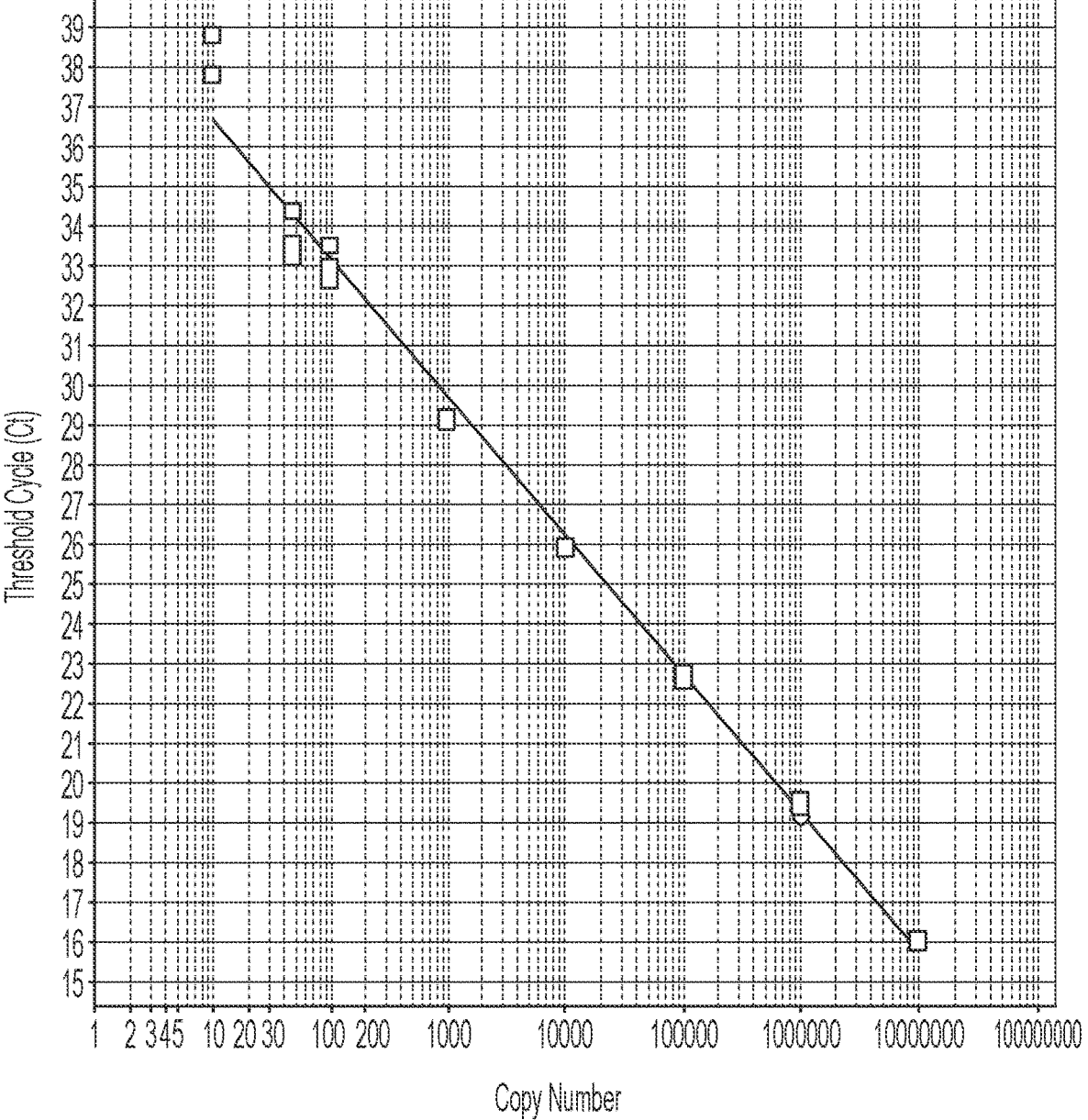
Figure 7C:
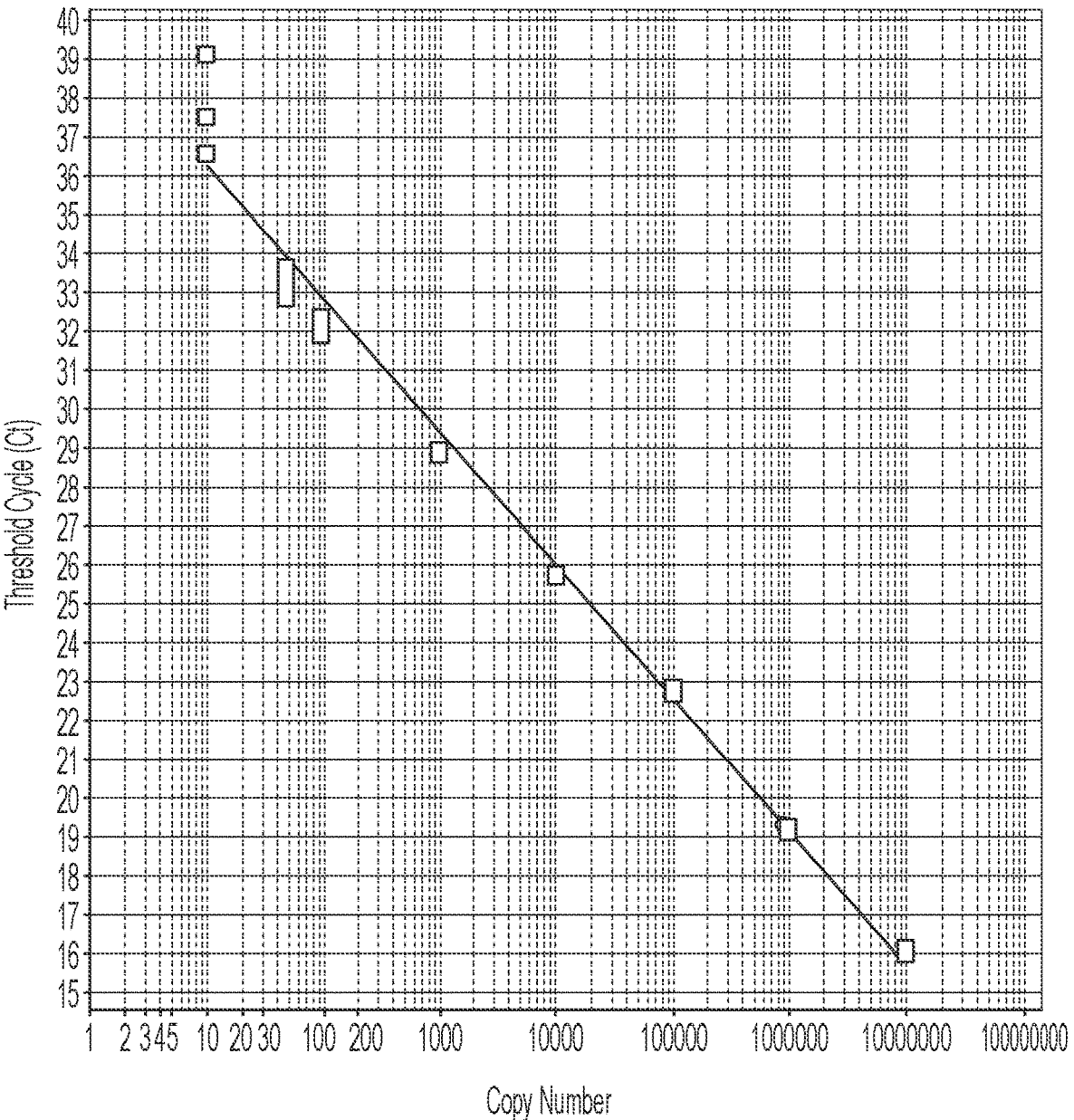
Figure 7D:
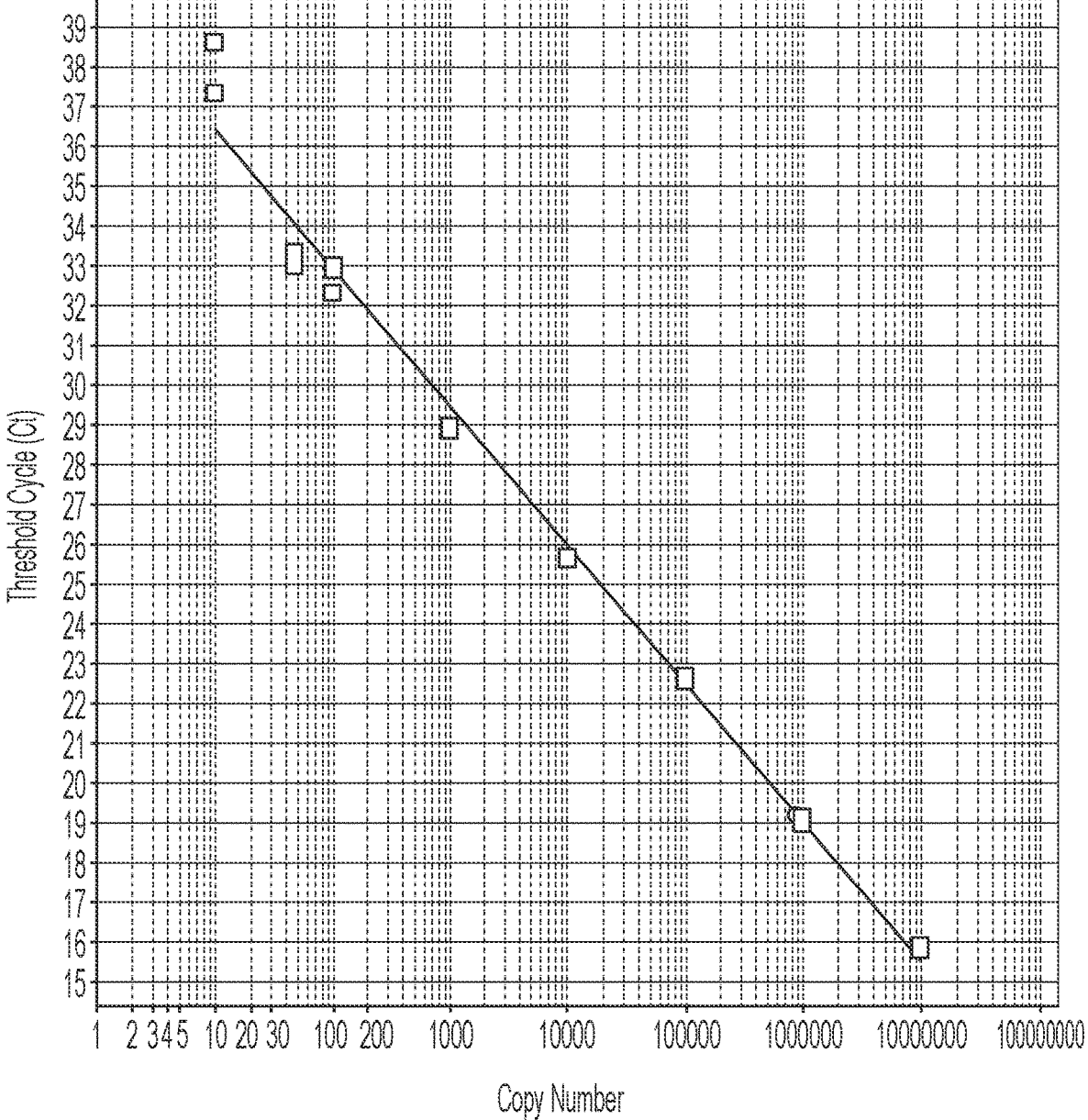

The standard curves of the primers/probe D1 in the presence of the 10-copy point and after removal of the 10-copy point are as shown in FIG. 4-2 and FIG. 4-3, respectively. Squares stand for a standard sample, the circles a test sample.

| Primer/probe name | Primers (μM) | Probe (μM) | Threshold | Efficiency | $R^2$ | Minimum copies |
|---|---|---|---|---|---|---|
| D1 | 0.9 | 0.25 | 0.1 | 87.745% | 0.993 | 10 |
| | 0.9 | 0.25 | 0.1 | 91.101% | 0.996 | 100 |

The data of the copy numbers will affect $R^2$ and the amplification efficiency of the entire standard curve. When the data of the 10-copy point were deleted, the amplification efficiency of the standard curve was good. It was considered to subsequently increase the minimum copy number point from 10 copies to 50 copies.

Example 4 D1 Primer Probe Test by TaqMan qPCR Under Different Primer Concentrations In the experiments, the primers were 0.9 μM, and the probe was 0.25 μM. It was tested whether changing the concentrations of the primers and/or probe (e.g., D1) could optimize the amplification efficiency. The experimental data for primer D1 at different concentrations are shown in FIGS. 5-1, 5-2 and 5-3.

The parameters of the D1 primers/probe set at different concentrations is shown below:

| Primer/probe name | Primers (μM) | Probe (μM) | Threshold | Efficiency | $R^2$ | 10 copies | $10^7$ copies |
|---|---|---|---|---|---|---|---|
| D1 | 1.8 | 0.5 | 0.1 | 79.293% | 0.994 | 38.903 | 16.027 |
| | 0.9 | 0.25 | 0.1 | 80.903% | 0.992 | 39.092 | 16.348 |
| | 0.45 | 0.125 | 0.1 | 87.102% | 0.994 | 38.289 | 16.728 |

$R^2$ was good with different concentrations of D1 primers/probe. However, the amplification efficiency was good only with low concentrations of the primers/probe.

Example 5 Effect of Different Concentrations of Background gDNA with Low Concentration of D1 Primer/Probe When low concentrations of the primers/probe were used, the amplification efficiency was high. In addition to the primer concentration, there exists the effect of the RNaseP in the experiment. Reducing the amount of background gDNA can improve the amplification efficiency of the reaction. Using low concentrations of the primers/probe, the impact of the background gDNA at different concentrations on the reaction was studied, with the standard curve being shown in FIGS. 6-1, 6-2 and 6-3. The parameters of the D1 primers/probe with different background gDNA concentrations are shown below:

| Primer/probe name | Primers (μM) | Probe (μM) | gDNA(ng) | Efficiency | $R^2$ | 50 copies | $10^7$ copies |
|---|---|---|---|---|---|---|---|
| D1 | 0.45 | 0.125 | 100 | 86.51% | 0.993 | 35.403 | 16.227 |
| | 0.45 | 0.125 | 50 | 94.112% | 0.998 | 34.838 | 16.578 |
| | 0.45 | 0.125 | 25 | 93.893% | 0.998 | 35.140 | 16.532 |

Thus, with 50 ng background gDNA, when the D1 primer/probe concentrations were halved (to 0.45 μM primers, 0.125 μM probe), $R^2$ and the amplification efficiency were good.

Example 6 Verification Experiment

1. Verification of the Standard Curve

The experimental results show that low concentrations of the D1 primers/probe combined with a 50 ng background gDNA produced excellent standard curve parameters in duplex reactions. Therefore, this condition was experimentally verified multiple times to eliminate the random errors of the experiment. The experimental results are shown in FIGS. 7A-7D.

The data of the four repeated experiments of D1 primers/probe with the 50 ng background gDNA at a half amount of DNA (0.45 μM primers, 0.125 μM probe) are as follows:

| Experiment | 1 | 2 | 3 | 4 |
|---|---|---|---|---|
| R2 | 0.998 | 0.999 | 0.999 | 0.999 |
| Eff % | 101.094 | 102.655 | 100.168 | 103.953 |
| Slope | −3.296 | −3.2599 | −3.3179 | −3.2307 |

In the four repeated experiments, the standard curve parameters all met the requirements and were relatively stable.

2. Verification of the Accuracy

From the above experimental data, it can be known that when standard curves are established, the linear parameters of the TaqMan detection method could meet the experimental requirements. In order to further verify the detection accuracy of the experimental plan, the quality control products prepared in advance at different copies were detected and the difference between the measured value and the theoretical value was compared to verify the accuracy of this detection plan and meanwhile determine the accuracy range of the detection.

The range of the copy numbers of the quality control product is determined according to the actually detected copy numbers and includes a higher limit of quantification (HLOQ), a high quality control (HQC), a medium-high quality control (MHQC), a medium quality control (MQC), a low quality control (LQC) and a lower limit of quantification (LLOQ). The corresponding copy numbers of the quality control products in 50 ng gDNA were $3.5\times10^4$, $1.75\times10^4$, 3500, 700, 140 and 28, respectively. The preparation method of the quality control products is shown below:

| | No. | — | — | HLOQ | HQC | — | — | MQC | — | — | LQC | — | — | LLOQ | — |
|---|---|---|---|---|---|---|---|---|---|---|---|---|---|---|---|
| | Concentration of the prepared plasmid solution copies/µL | $10^9$ | $10^8$ | $10^7$ | $5\times10^6$ | $10^6$ | $10^5$ | $5\times10^4$ | $10^4$ | $10^3$ | $5\times10^2$ | $10^2$ | 50 | 10 | 0 |
| Dilution process | Add Easy Dilution/µL | 90 | 90 | 90 | 30 | 90 | 90 | 30 | 90 | 90 | 30 | 90 | 30 | 90 | 30 |
| | Concentration of the added plasmid solution copies/µL | $10^{10}$ | $10^9$ | $10^8$ | $10^7$ | $10^7$ | $10^6$ | $10^5$ | $10^5$ | $10^4$ | $10^3$ | $10^3$ | $10^2$ | $10^2$ | — |
| | Volume of the added plasmid solution/µL | 10 | 10 | 10 | 30 | 10 | 10 | 30 | 10 | 10 | 30 | 10 | 30 | 10 | — |

The prepared quality control products were uniformly packaged, and were taken when they were tested to ensure the consistency of the quality control products and the independence of each testing experiment.

The accuracy verification experiment was carried out independently five times. The experimental results are as shown in Table 1 to Table 5:

TABLE 1

Results of standard curves of a TCR gene (linearity and amplification efficiency)
(Cq)

| Assay | | | Cq value | | | | | Amplification | |
|---|---|---|---|---|---|---|---|---|---|
| Assay | $1\times10^7$ | $1\times10^6$ | $1\times10^5$ | $1\times10^4$ | $1\times10^3$ | $1\times10^2$ | $R^2$ | efficiency (%) | Slope |
| Assay 1 | 16.38 | 19.71 | 22.98 | 26.04 | 29.54 | 33.61 | | | |
| 20190725 | 16.4 | 19.84 | 23.16 | 26.06 | 29.35 | 34.49 | | | |
| | 16.48 | 19.88 | 23.12 | 26.14 | 29.21 | 32.69 | | | |
| Mean value | 16.418 | 19.81 | 23.08 | 26.08 | 29.37 | 33.6 | 0.994 | 98.5 | −3.3 |
| Standard deviation | 0.06 | 0.09 | 0.09 | 0.06 | 0.17 | 0.9 | | | |
| Within-run precision (%) | 0.35 | 0.45 | 0.4 | 0.21 | 0.57 | 2.68 | | | |
| Assay2 | 16.39 | 19.6 | 22.98 | 26 | 29.4 | 33.47 | | | |
| 20190729 | 16.39 | 19.76 | 22.99 | 26.09 | 29.5 | 32.75 | | | |
| | 16.42 | 19.82 | 23.06 | 26.06 | 29.38 | 32.68 | | | |
| Mean value | 16.4 | 19.73 | 23.01 | 26.05 | 29.43 | 32.96 | 0.999 | 101.6 | −3.3 |
| Standard deviation | 0.02 | 0.12 | 0.04 | 0.05 | 0.06 | 0.44 | | | |
| Within-run precision (%) | 0.09 | 0.59 | 0.19 | 0.19 | 0.21 | 1.32 | | | |
| Assay3 | 16.67 | 19.86 | 23.28 | 26.3 | 30 | 34.39 | | | |
| 20190801 | 16.68 | 20.03 | 23.38 | 26.44 | 30.04 | 35.24 | | | |
| | 16.7 | 20.07 | 23.34 | 26.51 | 29.87 | 34.56 | | | |

TABLE 1-continued

Results of standard curves of a TCR gene (linearity and amplification efficiency)
(Cq)

| Assay | $1 \times 10^7$ | $1 \times 10^6$ | $1 \times 10^5$ | $1 \times 10^4$ | $1 \times 10^3$ | $1 \times 10^2$ | $R^2$ | Amplification efficiency (%) | Slope |
|---|---|---|---|---|---|---|---|---|---|
| | | | | Cq value | | | | | |
| Mean value | 16.69 | 19.99 | 23.33 | 26.42 | 29.97 | 34.73 | 0.994 | 92.3 | −3.5 |
| Standard deviation | 0.02 | 0.11 | 0.05 | 0.11 | 0.09 | 0.45 | | | |
| Within-run precision (%) | 0.09 | 0.55 | 0.2 | 0.41 | 0.3 | 1.29 | | | |
| Assay4 | 15.88 | 19.1 | 22.51 | 25.69 | 29.21 | 32.41 | | | |
| 20190814-1 | 15.74 | 19.25 | 22.57 | 25.65 | 29.07 | 32.6 | | | |
| | 15.92 | 19.34 | 22.59 | 25.64 | 28.87 | | 0.999 | 100.7 | −3.3 |
| Mean value | 15.85 | 19.23 | 22.56 | 25.66 | 29.05 | 32.51 | | | |
| Standard deviation | 0.09 | 0.12 | 0.04 | 0.03 | 0.17 | 0.13 | | | |
| Within-run precision (%) | 0.57 | 0.62 | 0.18 | 0.12 | 0.59 | 0.4 | | | |
| Assay5 | 15.89 | 19.23 | 22.54 | 25.71 | 28.78 | 31.79 | | | |
| 20190814-2 | 15.77 | 19.23 | 22.45 | 25.74 | 28.79 | 32.55 | | | |
| | 15.79 | 19.09 | 22.57 | 25.78 | 28.93 | 32.72 | | | |
| Mean value | 15.81 | 19.18 | 22.52 | 25.74 | 28.83 | 32.35 | 0.994 | 95.9 | −3.4 |
| Standard deviation | 0.07 | 0.08 | 0.06 | 0.03 | 0.08 | 0.5 | | | |
| Within-run precision (%) | 0.44 | 0.42 | 0.27 | 0.12 | 0.28 | 1.55 | | | |
| Mean value | 16.23 | 19.59 | 22.9 | 25.99 | 29.33 | 33.28 | | | |
| Standard deviation | 0.36 | 0.35 | 0.33 | 0.28 | 0.41 | 1.02 | | / | |
| Between-run precision (%) | 2.21 | 1.76 | 1.44 | 1.09 | 1.41 | 3.07 | | | |

TABLE 2

RNaseP precision verification results of standard curves (Cq)

| Assay | $1 \times 10^7$ | $1 \times 10^6$ | $1 \times 10^5$ | $1 \times 10^4$ | $1 \times 10^3$ | $1 \times 10^2$ |
|---|---|---|---|---|---|---|
| | | | Cq value | | | |
| Assay1 | 24.67 | 24.25 | 24.53 | 24.58 | 24.56 | 24.52 |
| 20190725 | 24.86 | 24.31 | 24.52 | 24.57 | 24.69 | 24.6 |
| | 24.75 | 24.29 | 24.41 | 24.54 | 24.59 | 24.67 |
| Mean value | | | 24.55 | | | |
| Standard deviation | | | 0.16 | | | |
| Within-run precision (%) | | | 0.64 | | | |
| Assay2 | 24.53 | 24.18 | 24.45 | 24.44 | 24.53 | 24.52 |
| 20190729 | 24.68 | 24.26 | 24.35 | 24.52 | 24.57 | 24.58 |
| | 24.65 | 24.28 | 24.4 | 24.5 | 24.57 | 24.66 |
| Mean value | | | 24.48 | | | |
| Standard deviation | | | 0.14 | | | |
| Within-run precision (%) | | | 0.58 | | | |
| Assay3 | 25.74 | 24.09 | 24.2 | 24.23 | 24.26 | 24.31 |
| 20190801 | 25.63 | 24.15 | 24.2 | 24.21 | 24.34 | 24.29 |
| | 25.64 | 24.16 | 24.07 | 24.17 | 24.28 | 24.36 |
| Mean value | | | 24.46 | | | |
| Standard deviation | | | 0.56 | | | |

TABLE 2-continued

RNaseP precision verification results of standard curves (Cq)

| Assay | $1 \times 10^7$ | $1 \times 10^6$ | $1 \times 10^5$ | $1 \times 10^4$ | $1 \times 10^3$ | $1 \times 10^2$ |
|---|---|---|---|---|---|---|
| | | | Cq value | | | |
| Within-run precision (%) | | | 2.3 | | | |
| Assay4 | 24.59 | 24.12 | 24.36 | 24.48 | 24.56 | 24.55 |
| 20190814-1 | 24.57 | 24.22 | 24.35 | 24.52 | 24.67 | 24.54 |
| | 24.56 | 24.22 | 24.36 | 24.49 | 24.61 | |
| Mean value | | | 24.46 | | | |
| Standard deviation | | | 0.16 | | | |
| Within-run precision (%) | | | 0.64 | | | |
| Assay5 | 24.39 | 24.07 | 24.3 | 24.58 | 24.52 | 24.54 |
| 20190814-2 | 24.44 | 24.09 | 24.29 | 24.59 | 24.54 | 24.6 |
| | 24.37 | 23.98 | 24.45 | 24.54 | 24.53 | 24.58 |
| Mean value | | | 24.41 | | | |
| Standard deviation | | | 0.19 | | | |
| Within-run precision (%) | | | 0.79 | | | |
| Mean value | | | 24.47 | | | |
| Standard deviation | | | 0.29 | | | |
| Within-run precision (%) | | | 0.18 | | | |

TABLE 3

Results of the precision and accuracy of the TCR gene
(copy number/50 ng gDNA reaction)

| Assay | Subject | HLOQ 3.5*$10^4$ | HQC 1.75*$10^4$ | MHQC 3500 | MQC 700 | LQC 140 | LLOQ 28 |
|---|---|---|---|---|---|---|---|
| | | | Theoretical copy number/50 ng gDNA reaction | | | | |
| Assay 1 | Copy number/ | 38,358.50 | 20,910.80 | 4,356.20 | 971.3 | 192.7 | 9.5 |
| 20190725 | reaction | 36,718.40 | 20,120.30 | 4,830.70 | 987.6 | 147.1 | 21.7 |

TABLE 3-continued

Results of the precision and accuracy of the TCR gene
(copy number/50 ng gDNA reaction)

| Assay | Subject | Theoretical copy number/50 ng gDNA reaction | | | | | |
|---|---|---|---|---|---|---|---|
| | | HLOQ 3.5*10^4 | HQC 1.75*10^4 | MHQC 3500 | MQC 700 | LQC 140 | LLOQ 28 |
| | | 37,239.00 | 21,222.50 | 4,889.00 | 1,174.30 | 170.3 | 19.4 |
| | | 38,258.40 | 20,459.20 | 4,543.50 | 1,005.00 | 118.2 | 21.7 |
| | Mean value | 37,643.60 | 20,678.20 | 4,654.80 | 1,034.60 | 157.1 | 18.1 |
| | Standard deviation | 797.6 | 486.4 | 249.9 | 94.2 | 31.9 | 5.8 |
| | Within-run precision (%) | 2.1 | 2.3 | 5.4 | 9.1 | 20.3 | 32.1 |
| | Within-run accuracy (%) | 107.6 | 118.2 | 133 | 147.8 | 95.5 | 112.2 |
| Assay 2 201 90729 | Copy number/ reaction | 32,226.20 | 16,987.30 | 4,012.90 | 868.8 | 113.5 | 5.9 |
| | | 30,805.40 | 16,709.80 | 3,909.60 | 623.1 | 87.1 | 15.4 |
| | | 31,628.70 | 17,413.90 | 3,815.70 | 765.4 | 150.5 | 2.8 |
| | | 31,120.30 | 16,663.40 | 4,108.60 | 828.2 | 76.8 | 34.2 |
| | Mean value | 31,445.20 | 16,943.60 | 3,961.70 | 771.4 | 107 | 14.6 |
| | Standard deviation | 621.4 | 344.6 | 126.8 | 107.6 | 32.9 | 14.1 |
| | Within-run precision (%) | 2 | 2 | 3.2 | 13.9 | 30.7 | 96.6 |
| | Within-run accuracy (%) | 89.8 | 96.8 | 113.2 | 110.2 | 76.4 | 52 |
| Assay 3 20190801 | Copy number/ reaction | 36,433.70 | 21,492.60 | 4,373.70 | 919.3 | 114 | 2.5 |
| | | 36,152.90 | 21,150.80 | 4,536.90 | 953.8 | 129 | 10.2 |
| | | 35,562.90 | 20,388.70 | 4,591.50 | 990.2 | 79.1 | |
| | | 35,266.90 | 20,742.10 | 4,692.40 | 750.2 | 100.6 | |
| | Mean value | 35,854.10 | 20,943.60 | 4,548.60 | 903.4 | 105.7 | 6.3 |
| | Standard deviation | 533.8 | 480.6 | 133.2 | 106.1 | 21.2 | 5.4 |
| | Within-run precision (%) | 1.5 | 2.3 | 2.9 | 11.7 | 20 | 85.7 |
| | Within-run accuracy (%) | 102.4 | 119.7 | 130 | 129 | 75.5 | 22.7 |
| Assay 4 20190814-1 | Copy number/ reaction | 32,483.30 | 18,501.20 | 4,021.40 | 688.9 | 107.3 | 25.4 |
| | | 31,768.70 | 17,475.30 | 4,107.60 | 716.8 | 132.8 | 8.4 |
| | | 34,677.10 | 17,897.90 | 3,903.40 | 629.1 | 107.4 | 12.3 |
| | | 31,727.20 | 17,862.00 | 4,278.50 | 905 | 133.1 | 33.2 |
| | Mean value | 32,664.10 | 17,934.10 | 4,077.70 | 735 | 120.1 | 19.8 |
| | Standard deviation | 1,386.20 | 423.7 | 157.9 | 119.1 | 14.8 | 11.5 |
| | Within-run precision (%) | 4.2 | 2.4 | 3.9 | 16.2 | 12.3 | 58.1 |
| | Within-run accuracy (%) | 93.3 | 102.5 | 116.5 | 105 | 85.8 | 70.7 |
| Assay 5 20190814-2 | Copy number/ reaction | 29,524.80 | 18,005.40 | 4,112.90 | 851.2 | 153.2 | 28.9 |
| | | 27,731.40 | 17,201.40 | 4,547.20 | 844.8 | 146.3 | 15.7 |
| | | 29,260.80 | 17,945.00 | 4,101.30 | 924.4 | 171.7 | 17.4 |
| | | 32,551.90 | 17,397.10 | 4,383.30 | 842.4 | 85.2 | 42.1 |
| | Mean value | 29,767.20 | 17,637.20 | 4,286.20 | 865.7 | 139.1 | 26 |
| | Standard deviation | 2,017.80 | 399.1 | 217.4 | 39.3 | 37.5 | 12.2 |
| | Within-run precision (%) | 6.8 | 2.3 | 5.1 | 4.5 | 27 | 46.9 |
| | Within-run accuracy (%) | 85 | 100.8 | 122.5 | 123.7 | 99.4 | 92.9 |
| | Mean value | 33474.8 | 18827.3 | 4305.8 | 862 | 125.8 | 18.2 |
| | Standard deviation | 3146.9 | 1738.8 | 317.2 | 138.7 | 32.7 | 11.3 |
| | Between-run precision (%) | 9.4 | 9.2 | 7.4 | 16.1 | 26 | 62.2 |
| | Between-run accuracy (%) | 95.6 | 107.6 | 123 | 123.1 | 89.9 | 64.8 |

TABLE 4

| Verification results of the precision and accuracy of the TCR gene (Cq) | | | | | | |
|---|---|---|---|---|---|---|
| Assay | Subject | HLOQ | HQC | MHQC | MQC | LQC | LLOQ |
| Assay 1 | Cq | 24.97 | 25.78 | 28.21 | 30.6 | 33.79 | 39.61 |
| 20190801 | | 24.98 | 25.8 | 28.16 | 30.54 | 33.6 | 37.49 |
| | | 25.01 | 25.86 | 28.14 | 30.49 | 34.35 | |
| | | 25.02 | 25.83 | 28.1 | 30.91 | 33.98 | |
| | Mean value | 25 | 25.82 | 28.15 | 30.63 | 33.93 | 38.55 |
| | Standard deviation | 0.02 | 0.04 | 0.05 | 0.19 | 0.32 | 1.5 |
| | Within-run precision (%) | 0.08 | 0.15 | 0.18 | 0.62 | 0.94 | 3.89 |
| Assay 2 | Cq | 24.44 | 25.33 | 27.62 | 29.81 | 32.17 | 36.55 |
| 20190725 | | 24.51 | 25.39 | 27.47 | 29.78 | 32.56 | 35.35 |
| | | 24.49 | 25.31 | 27.45 | 29.53 | 32.35 | 35.51 |
| | | 24.45 | 25.36 | 27.56 | 29.76 | 32.88 | 35.35 |
| | Mean value | 24.47 | 25.35 | 27.52 | 29.72 | 32.49 | 35.69 |
| | Standard deviation | 0.03 | 0.03 | 0.08 | 0.13 | 0.31 | 0.58 |
| | Within-run precision (%) | 0.12 | 0.12 | 0.29 | 0.44 | 0.95 | 1.63 |
| Assay 3 | Cq | 24.57 | 25.48 | 27.54 | 29.72 | 32.63 | 36.85 |
| 20190729 | | 24.63 | 25.51 | 27.58 | 30.2 | 33 | 35.48 |
| | | 24.6 | 25.45 | 27.61 | 29.9 | 32.22 | 37.88 |
| | | 24.62 | 25.51 | 27.51 | 29.79 | 33.18 | 34.34 |
| | Mean value | 24.6 | 25.49 | 27.56 | 29.9 | 32.76 | 36.14 |
| | Standard deviation | 0.03 | 0.03 | 0.05 | 0.21 | 0.43 | 1.55 |
| | Within-run precision (%) | 0.12 | 0.12 | 0.18 | 0.7 | 1.31 | 4.29 |
| Assay 4 | Cq | 24.1 | 24.9 | 27.09 | 29.63 | 32.3 | 34.37 |
| 20190814-1 | | 24.13 | 24.99 | 27.07 | 29.57 | 31.99 | 35.95 |
| | | 24 | 24.95 | 27.14 | 29.76 | 32.3 | 35.41 |
| | | 24.13 | 24.95 | 27.01 | 29.24 | 31.99 | 33.98 |
| | Mean value | 24.09 | 24.95 | 27.08 | 29.55 | 32.14 | 34.93 |
| | Standard deviation | 0.06 | 0.03 | 0.06 | 0.22 | 0.18 | 0.91 |
| | Within-run precision (%) | 0.25 | 0.12 | 0.22 | 0.74 | 0.56 | 2.61 |
| Assay 5 | Cq | 24.33 | 25.06 | 27.26 | 29.6 | 32.15 | 34.63 |
| 20190814-2 | | 24.42 | 25.13 | 27.11 | 29.61 | 32.22 | 35.55 |
| | | 24.34 | 25.07 | 27.26 | 29.48 | 31.98 | 35.39 |
| | | 24.18 | 25.11 | 27.16 | 29.62 | 33.03 | 34.08 |
| | Mean value | 24.32 | 25.09 | 27.2 | 29.58 | 32.35 | 34.91 |
| | Standard deviation | 0.1 | 0.03 | 0.08 | 0.07 | 0.46 | 0.69 |
| | Within-run precision (%) | 0.41 | 0.12 | 0.29 | 0.24 | 1.42 | 1.98 |
| Mean value | | 24.5 | 25.3 | 27.5 | 29.9 | 32.7 | 35.8 |
| Standard deviation | | 0.3 | 0.3 | 0.4 | 0.4 | 0.7 | 1.5 |
| Between-run precision (%) | | 1.3 | 1.2 | 1.4 | 1.5 | 2.2 | 4.1 |

TABLE 5

Comparison by analysts

Theoretical copy number/50 ng gDNA reaction

| Batch | Subject | HLOQ 3.5*10$^4$ | HQC 1.75*10$^4$ | MHQC 3500 | MQC 700 | LQC 140 | LLOQ 28 |
|---|---|---|---|---|---|---|---|
| Analyst-1 20190801 | Copy number/ reaction | 36,433.7 | 21,492.6 | 4,373.7 | 919.3 | 114.0 | |
| | | 36,152.9 | 21,150.8 | 4,536.9 | 953.8 | 129.0 | 2.5 |
| | | 35,562.9 | 20,388.7 | 4,591.5 | 990.2 | 79.1 | 10.2 |
| | | 35,266.9 | 20,742.1 | 4,692.4 | 750.2 | 100.6 | |
| | Mean value | 35,854.1 | 20,943.6 | 4,548.6 | 903.4 | 105.7 | 6.3 |
| | Standard deviation | 533.8 | 480.6 | 133.2 | 106.1 | 21.2 | 5.4 |
| | Within-run precision (%) | 1.5 | 2.3 | 2.9 | 11.7 | 20 | 85.7 |
| | Within-run accuracy (%) | 102.4 | 119.7 | 130.0 | 129.0 | 75.5 | 22.7 |
| Analyst-2 20190802 | Copy number/ reaction | 33,434.7 | 17,447.0 | 3,878.7 | 873.5 | 77.7 | 28.3 |
| | | 33,584.6 | 18,531.2 | 4,075.2 | 934.3 | 142.9 | 5.5 |
| | | 33,687.7 | 17,996.1 | 3,981.9 | 934.0 | 97.8 | 17.4 |
| | Mean value | 33,569.0 | 17,991.5 | 3,978.6 | 913.9 | 106.1 | 17.1 |
| | Standard deviation | 127.2 | 542.1 | 98.3 | 35.0 | 33.4 | 11.4 |
| | Within-run precision (%) | 0.38 | 3.01 | 2.47 | 3.83 | 31.48 | 66.67 |
| | Within-run accuracy (%) | 95.91 | 102.81 | 113.67 | 130.56 | 75.79 | 61.07 |
| Mean value | | 34874.77 | 19678.36 | 4304.33 | 907.90 | 105.87 | 12.78 |
| Standard deviation | | 1280.54 | 1644.21 | 323.93 | 77.93 | 24.41 | 10.34 |
| Between-run precision (%) | | 3.67 | 8.36 | 7.53 | 8.58 | 23.06 | 80.90 |
| Between-run accuracy (%) | | 99.64 | 112.45 | 122.98 | 129.70 | 75.62 | 45.64 |

The dilution range of the standard TCR plasmid was initially designed to be 10 to $1\times10^7$. Due to the impact of the reference gene for duplex reactions, the sensitivity decreased slightly. Meanwhile, in the initial accuracy testing experiments, it was determined that the lowest point should be $1\times10^2$. Thus, the standard TCR plasmid was diluted in a range of $1\times10^2$ to $1\times10^7$ copies/reaction. $R^2$ was in the range from 0.994 to 0.999, and the amplification efficiency was 92.3% to 101.6%. The within-run precision of each concentration point on the standard curve was 0.09% to 1.55%. The between-run precision was 1.09% to 3.07%. The within-run precision of the reference gene RNaseP was 0.58% to 2.30%, and the between-run precision was 1.18%. The linearity and precision were good and met the requirements of methodological verification.

The within-run accuracies of HLOQ, HQC, MHQC, MQC, LQC and LLOQ of TCR were 85.0% to 107.6%, 96.8% to 119.7%, 113.2% to 133.0%, 105.0% to 147.8%, 75.5% to 99.4% and 22.7% to 112.2%, respectively. The between-run accuracies of HLOQ, HQC, MHQC, MQC, LQC and LLOQ were 95.6%, 107.6%, 123.0%, 123.1%, 89.9% and 64.8%, respectively.

Calculated based on copy numbers, the within-run precisions of HLOQ, HQC, MHQC, MQC, LQC and LLOQ of TCR were 1.5% to 6.8%, 2.0% to 2.4%, 2.9% to 5.4%, 4.5% to 16.2%, 12.3% to 27% and 32.1% to 96.6%, respectively, and the between-run precisions were 9.4%, 9.2%, 7.4%, 16.1%, 26.0% and 62.2%, respectively.

Example 7 Determination of TCR Gene Copy Numbers in Patient's Blood Sample

The subject was a liver cancer patient of clinical trial NCT03971747. A blood sample was drawn on the 13th day after the patient received the anti-AFP TCR (murine) autologous T cell infusion which was used as a reference point for the baseline period. Blood samples were taken for testing on the day of the cell infusion and on the $4^{th}$, $7^{th}$, $10^{th}$, $14^{th}$, $21^{st}$ and $28^{th}$ days after the cell infusion. The copy numbers of mouse TCR with the PBMC genomic DNA in blood samples from each sampling point could reflect the dynamic amplification of AFP TCR-T cells at different time points in the patient. In clinical trials, this method was used to quantitatively determine the TCR gene copy number in the blood samples of patients receiving a T TCR (murine) autologous T cell therapy, thereby indirectly measuring the amplification of the TCR-T cells.

Figure 8:
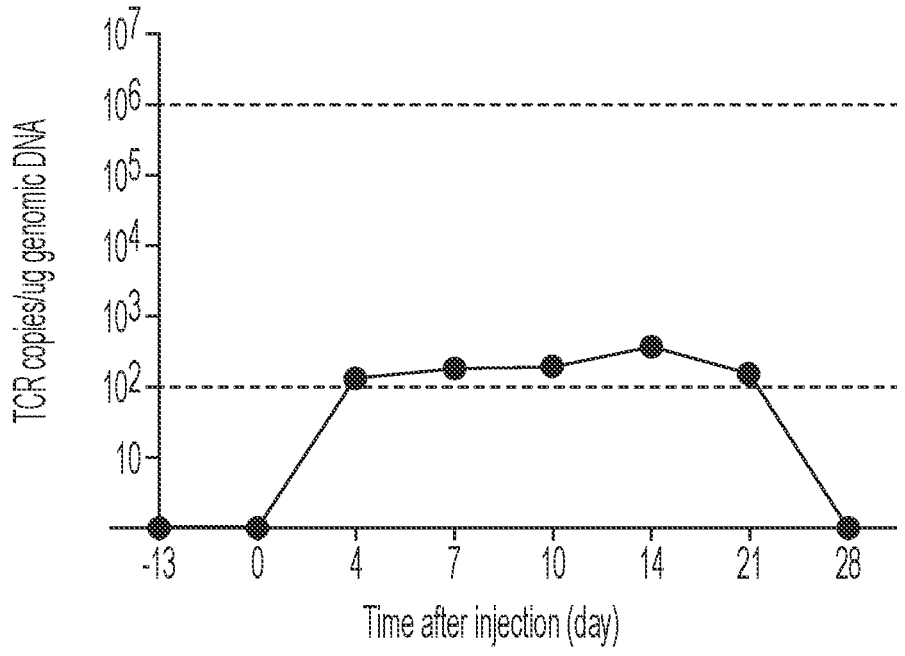
FIG. 8 shows the determination of TCR gene copy number in a blood sample of a patient receiving a mouse TCR-T cell therapy.

The experimental results are shown in Table 6 and FIG. 8.

TABLE 6

| Sampling time (day) | Ct value | Copy number before calibration | Calibration factor | Copy number after calibration |
|---|---|---|---|---|
| −13 | UND | 0 | 1.061 | 0 |
| 0 | UND | 0 | 0.79 | 0 |
| 4 | 35.254 | 169.4 | 0.79 | 135 |
| 7 | 36.479 | 213 | 0.84 | 179 |
| 10 | 35.468 | 233 | 0.84 | 196 |
| 14 | 34.483 | 415 | 0.90 | 373 |
| 21 | 34.864 | 160 | 0.85 | 136 |
| 28 | N/A | 0 | 0.85 | 0 |

UND: no signal detected.
N/A: Ct value greater than 35.

The results indicate that after the patient received intravenous infusion of low-dose AFP TCR-T cells, proliferation of the TCR-T cells in the body could be detected. This method can detect signals at a relatively low level. The results show that when a low dose of modified T cells was administered in a clinical trial, the amplification level of the T cells was low. It also shows that this detection method has relatively high sensitivity.

Example 8 Determining TCR Copy Numbers in
Tumors of Tumor-Bearing Mice

We also used this detection method to assay the tumor tissues of tumor-bearing mice injected with AFP TCR (murine)-T cells. The experimental mice were selected from the B-NDG strains from Biocytogen, and the tumor model was established by subcutaneous injection of HepG2 cells before growing for 5 days. On the 28th day after the injection of AFP TCR-T cells, the tumor tissue in the experimental mice was taken out and the mouse TCR gene of the genomic DNA was assayed.

The experimental results are as shown in Table 7.

TABLE 7

| Mouse No. | Group | Ct value | 28 days |
|---|---|---|---|
| 1-1 | Blank group | N/A | N/A |
| 1-2 | | N/A | N/A |
| 1-3 | | N/A | N/A |
| 2-1 | Low-dose group | N/A | N/A |
| 2-2 | | N/A | N/A |
| 2-3 | | N/A | N/A |
| 3-1 | Medium-dose group | N/A | N/A |
| 3-2 | | N/A | N/A |
| 3-3 | | N/A | N/A |
| 4-2 | High-dose group | 33.7 | 764 |
| 4-4 | | 31.1 | 4413 |
| 4-5 | | 34.4 | 514 |

UND: no signal detected.
N/A: Ct value is greater than 35.

The experimental results indicate that on the 28$^{th}$ day after injection, no signals were detected in the blank, low-dose and medium-dose groups. Copy numbers of mouse TCR were determined in the high-dose group. It shows that the modified T cells after injection can infiltrate the target solid tumor tissue and exert an effect.

SUMMARY

When TCR gene copy numbers are detected by the TaqMan method, the D1 primers/probe set may be used to establish standard curves. For RNaseP duplex reactions, 10, 50 or 100 copies may be used as the lowest copy number points of the standard curves. This may be decided based on the test results.

In certain embodiments, when the amount of the background gDNA is 50 ng, for the D1 primers/probe set, the primer concentration is 0.45 μM and the probe concentration is 0.125 μM.

Further, this method can be used clinically and has high sensitivity.

The scope of the present disclosure is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present disclosure and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present disclosure have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A system for determining a copy number of a mouse T cell receptor (TCR) gene, the system comprising (i) a forward primer comprising the nucleic acid sequence set forth in SEQ ID NO:1 and (ii) a reverse primer comprising the nucleic acid sequence set forth in SEQ ID NO:2, and (iii) a probe comprising a detectable label.

2. The system of claim 1, wherein the detectable label is a fluorescent label.

3. The system of claim 1, wherein the probe comprises the nucleic acid sequence set forth in SEQ ID NO: 3.

4. The system of claim 2, wherein the fluorescent label comprises a fluorescent reporter and a fluorescent quencher.

5. The system of claim 4, wherein the fluorescent reporter is at a 5' end of the probe, and wherein the fluorescent quencher is at a 3' end of the probe.

6. The system of claim 4, wherein the fluorescent reporter is at a 3' end of the probe, and wherein the fluorescent quencher is at a 5' end of the probe.

7. A method for determining a copy number of a mouse T cell receptor (TCR) gene in a sample, the method comprising:

(a) contacting the sample with the system of claim 1; and (b) conducting a nucleic acid amplification reaction.

8. A kit for determining a copy number of a mouse T cell receptor (TCR) gene, the kit comprising:

(i) a forward primer comprising a nucleic acid sequence set forth in SEQ ID NO:1 and (ii) a reverse primer comprising a nucleic acid sequence set forth in SEQ ID NO:2, and (iii) a probe comprising a detectable label.

9. The kit of claim 8, wherein the detectable label is a fluorescent label.

10. The kit of claim 8, wherein the probe comprises the nucleic acid sequence set forth in SEQ ID NO: 3.

11. The kit of claim 9, wherein the fluorescent label comprises a fluorescent reporter and a fluorescent quencher.

12. The method of claim 7, wherein the mouse TCR gene is a transgene.

13. The method of 9, wherein the nucleic acid amplification reaction is polymerase chain reaction (PCR).

* * * * *